(12) United States Patent
Van Ryn et al.

(10) Patent No.: US 8,486,398 B2
(45) Date of Patent: Jul. 16, 2013

(54) ANTICOAGULANT ANTIDOTES COMPRISING ANTIBODIES THAT BIND DABIGATRAN AND/OR RELATED COMPOUNDS

(75) Inventors: Joanne Van Ryn, Warthausen (DE);
John Edward Park, Warthausen (DE);
Norbert Hauel, Schemmerhofen (DE);
Ulrich Kunz, Biberach (DE); Tobias Litzenburger, Mittelbiberach (DE);
Keith Canada, Southbury, CT (US);
Sanjaya Singh, Sandy Hook, CT (US);
Alisa Waterman, Weston, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 38 days.

(21) Appl. No.: 13/010,403

(22) Filed: Jan. 20, 2011

(65) Prior Publication Data
US 2012/0027780 A1 Feb. 2, 2012

Related U.S. Application Data

(60) Provisional application No. 61/383,914, filed on Sep. 17, 2010.

(30) Foreign Application Priority Data

Jan. 20, 2010 (EP) .................................. 10151239

(51) Int. Cl.
*A61K 39/395* (2006.01)

(52) U.S. Cl.
USPC .................. 424/133.1; 424/135.1; 424/141.1; 514/13.7; 514/14.4

(58) Field of Classification Search
None
See application file for complete search history.

(56) References Cited

U.S. PATENT DOCUMENTS

| | | | | | |
|---|---|---|---|---|---|
| 5,693,762 | A | * | 12/1997 | Queen et al. ............... | 530/387.3 |
| 5,910,573 | A | * | 6/1999 | Pluckthun et al. ......... | 530/387.3 |
| 6,440,417 | B1 | | 8/2002 | Thibaudeau et al. | |
| 6,469,039 | B1 | | 10/2002 | Hauel et al. | |
| 2004/0097547 | A1 | | 5/2004 | Taveras et al. | |
| 2009/0098119 | A1 | * | 4/2009 | Lu et al. ..................... | 424/133.1 |
| 2011/0206656 | A1 | | 8/2011 | Van Ryn et al. | |
| 2012/0027780 | A1 | | 2/2012 | Van Ryn et al. | |

FOREIGN PATENT DOCUMENTS

| | | |
|---|---|---|
| CA | 2 277 949 | 8/1998 |
| WO | WO-98 37075 | 8/1998 |
| WO | WO-2011 023653 | 3/2011 |
| WO | WO-2011 089183 | 7/2011 |

OTHER PUBLICATIONS

Herion et al., Blood. May 1985;65(5):1201-7.*
Schlaeppi et al., Eur J Biochem. Mar. 10, 1990;188(2):463-70.*
Prescrire Int. Jun. 2009;18(101):97-9.*
Colburn, W. A., "Specific antibodies and fab fragments to alter the pharmacokinetics and reverse the pharmacologic/toxicologic effects of drugs," Drug Metabolism Reviews, 1980, vol. 11, No. 2, pp. 223-262.
Hardin, J. S. et al., "Pharmacodynamics of a monoclonal antiphencyclidine fab with broad selectivity for phencyclidine-like drugs," The Journal of Pharmacology and Experimental Therapeutics, 1998, vol. 285, No. 3, pp. 1113-1122.
Hursting, M. J. et al., "Drug-specific fab therapy in drug overdose," Arch Pathol Lab Med., 1987, vol. 111, pp. 693-697.
Lapostolle, F. et al., "Assessment of digoxin antibody use in patients with elevated serum digoxin following chronic or acute exposure," Intensive Care Med, 2008, vol. 34, pp. 1448-1453.
Schulman, S. et al., "Anticoagulants and their reversal," Transfusion Medicine Reviews, Jan. 2007, vol. 21, No. 1, pp. 37-48.
Van Ryn, J. et al., "Dabigatran etexilate—a novel, reversible, oral direct thrombin inhibitor: Interpretation of coagulation assays and reversal of anticoagulant activity," Thromb Haemost, 2010, vol. 103, pp. 1116-1127.
Zikria, J. C. et al., "Oral anticoagulation with factor Xa and thrombin inhibitors: on the threshold of change," Current Opinion in Hematology, 2009, vol. 16, No. 5, pp. 347-356.
Eisert, W. G. et al., Arteriosclerosis, Thrombosis, and Vascular Biology, 2010, vol. 30, pp. 1885-1889.
International Search Report for PCT/EP2011/073025 dated Mar. 14, 2012.
International Search Report for PCT/EP2012/055397 dated May 30, 2012.
Van Ryn, J. et al., "Dabigatran anticoagulant activity is neutralized by an antibody selective to dabigatran in in vitro and in vivo models," JACC, Apr. 5, 2011, vol. 57, No. 14.
Written Opinion of the International Search Authority for PCT/EP2011 073025 dated Mar. 14, 2012.
Written Opinion of the International Searching Authority for PCT/EP2012/055397 dated May 30, 2012.
Van Ryn, J. et al., "Dabigatran etexilate—novel, reversible, oral direct thrombin inhibitor: interpretation of coagulation assays and reversal of anticoagulant activity," Thrombosis and Haemostasis, 2011, vol. 105, No. 3, pp. 570.

* cited by examiner

*Primary Examiner* — Michael Szperka
(74) *Attorney, Agent, or Firm* — Michael P. Morris; Wendy A. Petka

(57) ABSTRACT

The present invention relates to antibody molecules against anticoagulants, in particular dabigatran, and their use as antidotes of such anticoagulants.

31 Claims, 14 Drawing Sheets

Figure 5

ANTICOAGULANT ANTIDOTES COMPRISING ANTIBODIES THAT BIND DABIGATRAN AND/OR RELATED COMPOUNDS

RELATED APPLICATIONS

This application claims benefit from U.S. Provisional Application No. 61/383,914, filed on Sep. 17, 2010 and European Priority Application No. 10151239, filed Jan. 20, 2010, the contents of which are incorporated herein in their entireties. PCT Application No. PCT/EP2011050749, filed concurrently herewith on Jan. 20, 2011, is also incorporated by reference in its entirety.

BACKGROUND OF THE INVENTION

1. Technical Field

The present invention pertains to the field of medicine, in particular to the field of anticoagulant therapy.

2. Background Information

Anticoagulants are substances that prevent coagulation; that is, they stop blood from clotting. Anticoagulants are widely used in human therapy as a medication for thrombotic disorders, for example primary and secondary prevention of deep vein thrombosis, pulmonary embolism, myocardial infarctions and strokes in those who are predisposed.

An important class of oral anticoagulants acts by antagonizing the effects of vitamin K, for example the coumarins which include warfarin. A second class of compounds inhibit coagulation indirectly via a cofactor such as antithrombin III or heparin cofactor II. This includes several low molecular weight heparin products which catalyse the inhibition of predominantly factor Xa (and to a lesser degree thrombin) via antithrombin III (bemiparin, certoparin, dalteparin, enoxaparin, nadroparin, parnaparin, reviparin, tinzaparin), Smaller chain oligosaccharides (fondaparinux, idraparinux) inhibit only factor Xa via antithrombin III. Heparinoids (danaparoid, sulodexide, dermatan sulfate) act via both cofactors and inhibit both factor Xa and thrombin. A third class represents the direct inhibitors of coagulation. Direct factor Xa inhibitors include apixaban, edoxaban, otamixaban, rivaroxaban, and direct thrombin inhibitors include the bivalent hirudins (bivalirudin, lepirudin, desirudin), and the monovalent compounds argatroban and dabigatran.

As blood clotting is a biological mechanism to stop bleeding, a side effect of anticoagulant therapy may be unwanted bleeding events. It is therefore desirable to provide an antidote to be able to stop such anticoagulant-related bleeding events when they occur (Zikria and Ansell, Current Opinion in Hematology 2009, 16(5): 347-356). One way to achieve this is by neutralizing the activity of the anticoagulant compound present in the patient after administration.

Currently available anticoagulant antidotes are protamine (for neutralization of heparin) and vitamin K for neutralization of vitamin K antagonists like warfarin. Fresh frozen plasma and recombinant factor VIIa have also been used as non-specific antidotes in patients under low molecular weight heparin treatment, suffering from major trauma or severe hemorrhage (Lauritzen, B. et al, Blood, 2005, 607A-608A). Also reported are protamine fragments (U.S. Pat. No. 6,624,141) and small synthetic peptides (U.S. Pat. No. 6,200,955) as heparin or low molecular weight heparin antidotes; and thrombin muteins (U.S. Pat. No. 6,060,300) as antidotes for thrombin inhibitor. Prothrombin intermediates and derivatives have been reported as antidotes to hirudin and synthetic thrombin inhibitors (U.S. Pat. Nos. 5,817,309 and 6,086,871). For direct factor Xa inhibitors, inactive factor Xa analogs have been proposed as antidotes (WO2009042962). Furthermore, recombinant factor VIIa has been used to reverse the effect of indirect antithrombin III dependent factor Xa inhibitors such as fondaparinux and idraparinux (Bijsterveld, N R et al, Circulation, 2002, 106: 2550-2554; Bijsterveld, N R et al, British J. of Haematology, 2004 (124): 653-658). A review of methods of anticoagulant reversal is provided in Schulman and Bijsterveld, Transfusion Medicine Reviews 2007, 21(1): 37-48.

There is a need to provide improved antidotes for anticoagulant therapy, and in particular to provide antidotes for direct thrombin inhibitors like dabigatran for which no specific antidotes have been disclosed so far.

BRIEF SUMMARY OF THE INVENTION

In one aspect, the present invention relates to an antibody molecule capable of neutralizing the activity of an anticoagulant.

In a further aspect, the antibody molecule has binding specificity for the anticoagulant.

In a further aspect, the anticoagulant is a direct thrombin inhibitor, a Factor Xa inhibitor, or a vitamin K antagonist.

In a further aspect, the anticoagulant is dabigatran, argatroban, melagatran, ximelagatran, hirudin, bivalirudin, lepirudin, desirudin, apixaban, otamixaban, edoxaban, rivaroxaban, defibrotide, ramatroban, antithrombin III, or drotrecogin alpha.

In a further embodiment, the anticoagulant is a disubstituted bicyclic heterocycle of general formula

$$R_a\text{-A-Het-B—Ar-E}, \quad (I)$$

wherein

A denotes a carbonyl or sulphonyl group linked to the benzo, pyrido or thieno moiety of the group Het, B denotes an ethylene group in which the methylene group linked to the group Ar may be replaced by an oxygen or sulphur atom or by an —$NR_1$— group, wherein $R_1$ denotes a hydrogen atom or a $C_{1-4}$-alkyl group, E denotes an $R_b$NH—C(=NH)— group wherein $R_b$ denotes a hydrogen atom, a hydroxy, $C_{1-9}$-alkoxycarbonyl, cyclohexyloxycarbonyl, phenyl-$C_{1-3}$-alkoxycarbonyl, benzoyl, p-$C_{1-3}$-alkyl-benzoyl or pyridinoyl group, whilst the ethoxy moiety in the 2-position of the above-mentioned $C_{1-9}$-alkoxycarbonyl group may additionally be substituted by a $C_{1-3}$-alkylsulphonyl or 2-($C_{1-3}$-alkoxy)-ethyl group, Ar denotes a 1,4-phenylene group optionally substituted by a chlorine atom or by a methyl, ethyl or methoxy group or it denotes a 2,5-thienylene group, Het denotes a 1-($C_{1-3}$-alkyl)-2,5-benzimidazolylene, 1-cyclopropyl-2,5-benzimidazolylene, 2,5-benzothiazolylene, 1-($C_{1-3}$-alkyl)-2,5-indolylene, 1-($C_{1-3}$-alkyl)-2,5-imidazo[4,5-b]pyridinylene, 3-($C_{1-3}$-alkyl)-2,7-imidazo[1,2-a]pyridinylene or 1-($C_{1-3}$-alkyl)-2,5-thieno[2,3-d]imidazolylene group and $R_a$ denotes an $R_2NR_3$— group wherein $R_2$ is a $C_{1-4}$-alkyl group which may be substituted by a carboxy, $C_{1-6}$-alkyloxycarbonyl, benzyloxycarbonyl, $C_{1-3}$-alkylsulphonylaminocarbonyl or 1 H-tetrazol-5-yl group, a $C_{2-4}$-alkyl group substituted by a hydroxy, benzyloxy, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)-$C_{1-3}$-alkoxycarbonyl-$C_{1-3}$-alkylamino group, whilst in the abovementioned groups the carbon atom in the α-position to the adjacent nitrogen atom may not be substituted, R$_3$ denotes a C$_{3-7}$-cycloalkyl group, a propargyl group, wherein the unsaturated part may not be linked directly to the nitrogen atom of the R$_2$NR$_3$ group, a phenyl group optionally substituted by a fluorine or chlorine atom, or by a methyl or methoxy group, a pyrazolyl, pyridazolyl or pyridinyl group optionally substituted by a methyl group or R$_2$ and R$_3$ together with the nitrogen atom between them denote a 5- to 7-membered cycloalkyleneimino group, optionally substituted by a carboxy or C$_{1-4}$-alkoxycarbonyl group, to which a phenyl ring may additionally be fused, the tautomers, the stereoisomers and the salts thereof.

In a further embodiment, the anticoagulant is a compound selected from (a) 2-[N-(4-amidinophenyl)-aminomethyl]-benzthiazole-5-carboxylic acid-N-phenyl-N-(2-carboxyethyl)-amide,
(b) 2-[N-(4-amidinophenyl)-N-methyl-aminomethyl]-benzthiazol-5-yl-carboxylic acid-N-phenyl-N-(2-hydroxycarbonylethyl)-amide,
(c) 1-Methyl-2-[N-(4-amidinophenyl)-aminomethyl]-benzimidazol-5-yl-carboxylic acid-N-phenyl-N-(2-hydroxycarbonylethyl)-amide,
(d) 1-Methyl-2-[N-(4-amidinophenyl)-aminomethyl]-benzimidazol-5-yl-carboxylic acid-N-phenyl-N-(3-hydroxycarbonylpropyl)-amide,
(e) 1-Methyl-2-[N-(4-amidinophenyl)-aminomethyl]-benzimidazol-5-yl-carboxylic acid-N-(2-pyridyl)-N-(hydroxycarbonylmethyl)-amide,
(f) 1-Methyl-2-[2-(2-amidinothiophen-5-yl)ethyl]-benzimidazol-5-yl-carboxylic acid-N-(2-pyridyl)-N-(2-hydroxycarbonylethyl)-amide,
(g) 1-Methyl-2-[N-(4-amidinophenyl)-aminomethyl]-benzimidazol-5-yl-carboxylic acid-N-(2-pyridyl)-N-(2-hydroxycarbonylethyl)-amide,
(h) 1-Methyl-2-[2-(4-amidinophenyl)ethyl]-benzimidazol-5-yl-carboxylic acid-N-(2-pyridyl)-N-(2-hydroxycarbonylethyl)-amide,
(i) 1-Methyl-2-[2-(4-amidinophenyl)ethyl]-benzimidazol-5-yl-carboxylic acid-N-phenyl-N-(2-hydroxycarbonylethyl)-amide,
(j) 1-Methyl-2-[2-(4-amidinophenyl)ethyl]-benzimidazol-5-yl-carboxylic acid-N-phenyl-N-[2-(1H-tetrazol-5-yl)ethyl]-amide,
(k) 1-Methyl-2-[N-(4-amidinophenyl)-aminomethyl]-benzimidazol-5-yl-carboxylic acid-N-phenyl-N-[2-(1H-tetrazol-5-yl)ethyl]-amide,
(l) 1-Methyl-2-[N-(4-amidinophenyl)-N-methyl-aminomethyl]-benzimidazol-5-yl-carboxylic acid-N-(2-pyridyl)-N-(2-hydroxycarbonylethyl)-amide,
(m) 1-Methyl-2-[N-(4-amidinophenyl)-N-methyl-aminomethyl]-benzimidazol-5-yl-carboxylic acid-N-(3-pyridyl)-N-(2-hydroxycarbonylethyl)-amide,
(n) 1-Methyl-2-[N-(4-amidinophenyl)-N-methyl-aminomethyl]-benzimidazol-5-yl-carboxylic acid-N-phenyl-N-(2-hydroxycarbonylethyl)-amide,
(o) 1-Methyl-2-[N-(4-amidinophenyl)-aminomethyl]-benzimidazol-5-yl-carboxylic acid-N-phenyl-N-[(N-hydroxycarbonylethyl-N-methyl)-2-aminoethyl]-amide,
(p) 1-Methyl-2-[N-(4-amidinophenyl)-aminomethyl]-benzimidazol-5-yl-carboxylic acid-N-(3-fluorophenyl)-N-(2-hydroxycarbonylethyl)-amide,
(q) 1-Methyl-2-[N-(4-amidinophenyl)-aminomethyl]-benzimidazol-5-yl-carboxylic acid-N-(4-fluorophenyl)-N-(2-hydroxycarbonylethyl)-amide,
(r) 1-Methyl-2-[N-(4-amidino-2-methoxy-phenyl)-aminomethyl]-benzimidazol-5-yl-carboxylic acid-N-phenyl-N-(2-hydroxycarbonylethyl)-amide,
(s) 1-Methyl-2-[N-(4-amidino-2-methoxy-phenyl)-aminomethyl]-benzimidazol-5-yl-carboxylic acid-N-(2-pyridyl)-N-(2-hydroxycarbonylethyl)-amide,
(t) 1-Methyl-2-[N-(4-amidinophenyl)aminomethyl]-indol-5-yl-carboxylic acid-N-phenyl-N-(2-methoxycarbonylethyl)-amide,
(u) 1-Methyl-2-[N-(4-amidinophenyl)aminomethyl]-thieno[2,3-d]imidazol-5-yl-carboxylic acid-N-phenyl-N-(2-hydroxycarbonylethyl)-amide,
(v) 1-Methyl-2-[N-(4-amidinophenyl)-aminomethyl]-benzimidazol-5-yl-carboxylic acid-N-phenyl-N-(2-hydroxycarbonylethyl)-amide,
(w) 1-Methyl-2-[N-(4-amidinophenyl)-aminomethyl]-benzimidazol-5-yl-carboxylic acid-N-(2-pyridyl)-N-(2-hydroxycarbonylethyl)-amide,
(x) 1-Methyl-2-[N-(4-amidino-2-methoxy-phenyl)-aminomethyl]-benzimidazol-5-yl-carboxylic acid-N-(2-pyridyl)-N-(2-hydroxycarbonylethyl)-amide,
(y) 1-Methyl-2-[N-[4-(N-n-hexyloxycarbonylamidino)phenyl]-aminomethyl]-benzimidazol-5-yl-carboxylic acid-N-(2-pyridyl)-N-(2-ethoxycarbonylethyl)-amide, and the tautomers, stereoisomers and the salts thereof.

In another aspect, the present invention relates to an antibody molecule against dabigatran, dabigatran exetilate, and/or an O-acylglucuronide of dabigatran.

In a further aspect, the antibody molecule is a polyclonal antibody, a monoclonal antibody, a human antibody, a humanized antibody, a chimeric antibody, a fragment of an antibody, in particular a Fab, Fab', or F(ab')$_2$ fragment, a single chain antibody, in particular a single chain variable fragment (scFv), a domain antibody, a nanobody, a diabody, or a DARPin.

In a further aspect, the present invention relates to an antibody molecule as described above for use in medicine.

In a further aspect, the present invention relates to an antibody molecule as described above for use in the therapy or prevention of side effects of anticoagulant therapy.

In a further aspect, the side effect is a bleeding event.

In a further aspect, the present invention relates to a method of treatment or prevention of side effects of anticoagulant therapy, comprising administering an effective amount of an antibody molecule as described above to a patient in need thereof.

In another aspect, the present invention relates to a kit comprising an antibody molecule as described, together with a container and a label.

BRIEF DESCRIPTION OF THE DRAWINGS

FIG. 5: Sequences of variable regions of anti-dabigatran antibody molecule heavy chains Sequences correspond to SEQ ID numbers in the Listing as follows: DBG 13 VH=SEQ ID NO:16; DBG 14 VH=SEQ ID NO:18; DBG 22 VH=SEQ ID NO:20; ENG VH#14=SEQ ID NO:22; ENG VH#15=SEQ ID NO:24; ENG VH#31=SEQ ID NO:26.

DETAILED DESCRIPTION OF THE INVENTION

Figure 1:
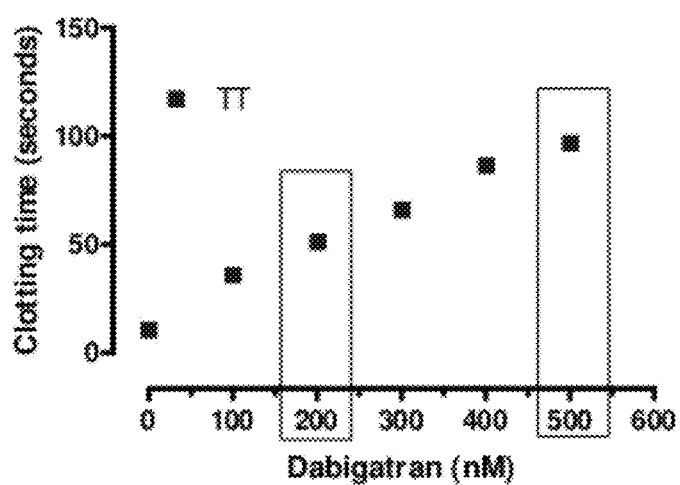
FIG. 1: Increased time to clotting seen with increased concentrations of dabigatran using the thrombin clotting time assay. The 200 nM concentration resulted in an ~5-fold elevation in clotting time over baseline and was used in the first and second set of experiments. The 500 nM concentration (supratherapeutic) was used in the last set of experiments.

In one aspect, the present invention relates to an antibody molecule capable of neutralizing the activity of an anticoagulant.

Antibodies (also known as immunoglobulins, abbreviated Ig) are gamma globulin proteins that can be found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibodies can bind, by non-covalent interaction, to other molecules or structures known as antigens. This binding is specific in the sense that an antibody will only bind to a specific structure with high affinity. The unique part of the antigen recognized by an antibody is called an epitope, or antigenic determinant. The part of the antibody binding to the epitope is sometimes called paratope and resides in the so-called variable domain, or variable region (Fv) of the antibody. The variable domain comprises three so-called complementary-determining region (CDR's) spaced apart by framework regions (FR's).

Within the context of this invention, reference to CDR's is based on the definition of Chothia (Chothia and Lesk, J. Mol. Biol. 1987, 196: 901-917), together with Kabat (E. A. Kabat, T. T. Wu, H. Bilofsky, M. Reid-Miller and H. Perry, Sequence of Proteins of Immunological Interest, National Institutes of Health, Bethesda (1983)).

The art has further developed antibodies and made them versatile tools in medicine and technology. Thus, in the context of the present invention the terms "antibody molecule" or "antibody" (used synonymously herein) do not only include antibodies as they may be found in nature, comprising e.g. two light chains and two heavy chains, or just two heavy chains as in camelid species, but furthermore encompasses all molecules comprising at least one paratope with binding specificity to an antigen and structural similarity to a variable domain of an immunoglobulin.

Thus, an antibody molecule according to the invention may be a polyclonal antibody, a monoclonal antibody, a human antibody, a humanized antibody, a chimeric antibody, a fragment of an antibody, in particular a Fv, Fab, Fab', or F(ab')$_2$ fragment, a single chain antibody, in particular a single chain variable fragment (scFv), a Small Modular Immunopharmaceutical (SMIP), a domain antibody, a nanobody, a diabody.

Polyclonal antibodies represent a collection of antibody molecules with different amino acid sequences and may be obtained from the blood of vertebrates after immunization with the antigen by processes well-known in the art.

Monoclonal antibodies (mAb or moAb) are monospecific antibodies that are identical in amino acid sequence. They may be produced by hybridoma technology from a hybrid cell line (called hybridoma) representing a clone of a fusion of a specific antibody-producing B cell with a myeloma (B cell cancer) cell (Kohler G, Milstein C. Continuous cultures of fused cells secreting antibody of predefined specificity. Nature 1975; 256:495-7). Alternatively, monoclonal antibodies may be produced by recombinant expression in host cells (Norderhaug L, Olafsen T, Michaelsen T E, Sandlie I. (May 1997). "Versatile vectors for transient and stable expression of recombinant antibody molecules in mammalian cells.". J Immunol Methods 204 (1): 77-87; see also below).

For application in man, it is often desirable to reduce immunogenicity of antibodies originally derived from other species, like mouse. This can be done by construction of chimeric antibodies, or by a process called "humanization". In this context, a "chimeric antibody" is understood to be an antibody comprising a sequence part (e.g. a variable domain) derived from one species (e.g. mouse) fused to a sequence part (e.g. the constant domains) derived from a different species (e.g. human). A "humanized antibody" is an antibody comprising a variable domain originally derived from a non-human species, wherein certain amino acids have been mutated to resemble the overall sequence of that variable domain more closely to a sequence of a human variable domain. Methods of chimerisation and -humanization of antibodies are well-known in the art (Billetta R, Lobuglio A F. "Chimeric antibodies". Int Rev Immunol. 1993; 10(2-3):165-76; Riechmann L, Clark M, Waldmann H, Winter G (1988). "Reshaping human antibodies for therapy". *Nature:* 332:323).

Furthermore, technologies have been developed for creating antibodies based on sequences derived from the human genome, for example by phage display or using transgenic animals (WO 90/05144; D. Marks, H.R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93; Bruggemann M, Taussig M J. "Production of human antibody repertoires in transgenic mice". Curr Opin Biotechnol. 1997 August; 8(4): 455-8). Such antibodies are "human antibodies" in the context of the present invention.

Antibody molecules according to the present invention also include fragments of immunoglobulins which retain antigen binding properties, like Fab, Fab', or F(ab')$_2$ fragments. Such fragments may be obtained by fragmentation of immunoglobulins e.g. by proteolytic digestion, or by recombinant expression of such fragments. For example, immunoglobulin digestion can be accomplished by means of routine techniques, e.g. using papain or pepsin (WO 94/29348), or endoproteinase Lys-C (Kleemann, et al, Anal. Chem. 80, 2001-2009, 2008). Papain or Lys-C digestion of antibodies typically produces two identical antigen binding fragments, so-called Fab fragments, each with a single antigen binding site, and a residual Fc fragment. Pepsin treatment yields an F(ab')$_2$. Methods of producing Fab molecules by recombinant expression in host cells are outlined in more detail below.

A number of technologies have been developed for placing variable domains of immunoglobulins, or molecules derived from such variable domains, in a different molecular context. Those should be also considered as "antibody molecules" in accordance with the present invention. In general, these antibody molecules are smaller in size compared to immunoglobulins, and may comprise a single amino acid chain or be composed of several amino acid chains. For example, a single-chain variable fragment (scFv) is a fusion of the variable regions of the heavy and light chains of immunoglobulins, linked together with a short linker, usually serine (S) or glycine (G) (WO 88/01649; WO 91/17271; Huston et al; International Reviews of Immunology, Volume 10, 1993, 195-217). "Single domain antibodies" or "nanobodies" harbour an antigen-binding site in a single Ig-like domain (WO 94/04678; WO 03/050531, Ward et al., Nature. 1989 Oct. 12; 341(6242):544-6; Revets et al., Expert Opin Biol Ther. 5(1): 111-24, 2005). One or more single domain antibodies with binding specificity for the same or a different antigen may be linked together. Diabodies are bivalent antibody molecules consisting of two amino acid chains comprising two variable domains (WO 94/13804, Holliger et al., Proc Natl Acad Sci USA. 1993 Jul. 15; 90(14):6444-8). Other examples for antibody-like molecules are immunoglobulin super family antibodies (IgSF; Srinivasan and Roeske, Current Protein Pept. Sci. 2005, 6(2): 185-96). A different concept leads to the so-called Small Modular Immunopharmaceutical (SMIP) which comprises a Fv domain linked to single-chain hinge and effector domains devoid of the constant domain CH1 (WO 02/056910).

In a further aspect, an antibody molecule of the invention may even only have remote structural relatedness to an immunoglobulin variable domain, or no such relation at all, as long as it has a certain binding specificity and affinity comparable to an immunoglobulin variable domain. Such non-immunoglobulin "antibody mimics", sometimes called "scaffold proteins", may be based on the genes of protein A, the lipocalins, a fibronectin domain, an ankyrin consensus repeat domain, and thioredoxin (Skerra, Current Opinion in Biotechnology 2007, 18(4): 295-304). A preferred embodiment in the context of the present invention are designed ankyrin repeat proteins (DARPin's; Steiner et al., J Mol. Biol. 2008 Oct. 24; 382(5): 1211-27; Stumpp M T, Amstutz P. Curr Opin Drug Discov Devel. 2007 March; 10(2):153-9).

The antibody molecule may be fused (as a fusion protein) or otherwise linked (by covalent or non-covalent bonds) to other molecular entities having a desired impact on the properties of the antibody molecule. For example, it may be desirable to improve pharmacokinetic properties of antibody molecules, stability e.g. in body fluids such as blood, in particular in the case of single chain antibodies or domain antibodies. A number of technologies have been developed in this regard, in particular to prolong half-life of such antibody molecules in the circulation, such as pegylation (WO 98/25971; WO 98/48837; WO 2004081026), fusing or otherwise covalently attaching the antibody molecule to another antibody molecule having affinity to a serum protein like albumin (WO 2004041865; WO 2004003019), or expression of the antibody molecule as fusion protein with all or part of a serum protein like albumin or transferrin (WO 01/79258).

In a further aspect, the antibody molecule has binding specificity for the anticoagulant. "Binding specificity" means that the antibody molecule has a significantly higher binding affinity to the anticoagulant than to structurally unrelated molecules.

Affinity is the interaction between a single antigen-binding site on an antibody molecule and a single epitope. It is expressed by the association constant $K_A = k_{ass}/k_{diss}$, or the dissociation constant $K_D = k_{diss}/k_{ass}$.

In one aspect of the invention, the antibody binds to the anticoagulant with an affinity, as determined e.g. by surface plasmon resonance analysis (Malmqvist M., "Surface plasmon resonance for detection and measurement of antibody-antigen affinity and kinetics.", Curr Opin Immunol. 1993 April; 5(2):282-6), with a $K_D$ value ranging from 0.1 pM to 100 µM, preferably 1 pM to 100 µM, preferably 1 pM to 1 µM. Antibody affinity can also be measured using kinetic exclusion assay (KinExA) technology (Darling, R. J., and Brault P-A., "Kinetic exclusion assay technology: Characterization of Molecular Interactions." ASSAY and Drug Development Technologies. 2004, December 2(6): 647-657).

The binding affinity of an antibody molecule may be enhanced by a process known as affinity maturation (Marks et al., 1992, Biotechnology 10:779-783; Barbas, et al., 1994, Proc. Nat. Acad. Sci, USA 91:3809-3813; Shier et al., 1995, Gene 169:147-155). Affinity matured antibodies are therefore also embraced in the present invention.

In a further aspect of the invention, the antibody molecule is capable of neutralizing the activity of the anticoagulant. That is, upon binding to the antibody molecule, the anticoagulant is no longer able to exert its anticoagulant activity, or exerts this activity at a significantly decreased magnitude. Preferably, the anticoagulant activity is decreased at least 2fold, 5fold, 10fold, or 100fold upon antibody binding, as determined in an activity assay which is appropriate for the anticoagulant at issue, particularly a clotting assay that is sensitive to thrombin, such as the ecarin clotting time or the thrombin clotting time (H. Bounameaux, Marbet G A, Lammle B, et al. "Monitoring of heparin treatment. Comparison of thrombin time, activated partial thromboplastin time, and plasma heparin concentration, and analysis of the behaviour of antithrombin III". American Journal of Clinical Pathology 1980 74(1): 68-72).

For manufacturing the antibody molecules of the invention, the skilled artisan may choose from a variety of methods well known in the art (Norderhaug et al., J Immunol Methods 1997, 204 (1): 77-87; Kipriyanow and Le Gall, Molecular Biotechnology 26: 39-60, 2004; Shukla et al., 2007, J. Chromatography B, 848(1): 28-39).

Anticoagulants are well-known in the art, as outlined above. In a further aspect of the invention, the anticoagulant is a direct thrombin inhibitor, a Factor Xa inhibitor, or a vitamin K antagonist. Examples of vitamin K antagonists are the coumarins, which include warfarin. Examples of indirect predominantly factor Xa inhibitors are the heparin group of substances acting through activation of antithrombin III including several low molecular weight heparin products (bemiparin, certoparin, dalteparin, enoxaparin, nadroparin, parnaparin, reviparin, tinzaparin), certain oligosaccharides (fondaparinux, idraparinux), heparinoids (danaparoid, sulodexide, dermatan sulfate), and the direct factor Xa inhibitors (apixaban, otamixaban, rivaroxaban). Examples of thrombin inhibitors include the bivalent hirudins (bivalirudin, lepirudin, desirudin), and the monovalent compounds argatroban and dabigatran.

Thus, in a further aspect, the anticoagulant is dabigatran, argatroban, melagatran, ximelagatran, hirudin, bivalirudin, lepirudin, desirudin, apixaban, edoxaban, otamixaban, rivaroxaban, defibrotide, ramatroban, antithrombin III, or drotrecogin alpha.

In a further embodiment, the anticoagulant is a disubstituted bicyclic heterocycle of general formula

$$R_a\text{-A-Het-B}-\text{Ar-E}, \quad (I)$$

wherein

A denotes a carbonyl or sulphonyl group linked to the benzo, pyrido or thieno moiety of the group Het, B denotes an ethylene group in which the methylene group linked to the group Ar may be replaced by an oxygen or sulphur atom or by an —NR₁— group, wherein
  R₁ denotes a hydrogen atom or a $C_{1-4}$-alkyl group, E denotes an $R_bNH$—C(=NH)— group wherein
  $R_b$ denotes a hydrogen atom, a hydroxy, $C_{1-9}$-alkoxycarbonyl, cyclohexyloxycarbonyl, phenyl-$C_{1-3}$-alkoxycarbonyl, benzoyl, p-$C_{1-3}$-alkyl-benzoyl or pyridinoyl group, whilst the ethoxy moiety in the 2-position of the above-mentioned $C_{1-9}$-alkoxycarbonyl group may additionally be substituted by a $C_{1-3}$-alkylsulphonyl or 2-($C_{1-3}$-alkoxy)-ethyl group, Ar denotes a 1,4-phenylene group optionally substituted by a chlorine atom or by a methyl, ethyl or methoxy group or it denotes a 2,5-thienylene group, Het denotes a 1-($C_{1-3}$-alkyl)-2,5-benzimidazolylene, 1-cyclopropyl-2,5-benzimidazolylene, 2,5-benzothiazolylene, 1-($C_{1-3}$-alkyl)-2,5-indolylene, 1-($C_{1-3}$-alkyl)-2,5-imidazo[4,5-b]pyridinylene, 3-($C_{1-3}$-alkyl)-2,7-imidazo[1,2-a]pyridinylene or 1-($C_{1-3}$-alkyl)-2,5-thieno[2,3-d]imidazolylene group and $R_a$ denotes an $R_2NR_3$— group wherein
  $R_2$ is a $C_{1-4}$-alkyl group which may be substituted by a carboxy, $C_{1-6}$-alkyloxycarbonyl, benzyloxycarbonyl, $C_{1-3}$-alkylsulphonylaminocarbonyl or 1H-tetrazol-5-yl group, a $C_{2-4}$-alkyl group substituted by a hydroxy, benzyloxy, carboxy-$C_{1-3}$-alkylamino, $C_{1-3}$-alkoxycarbonyl-$C_{1-3}$-alkylamino, N—($C_{1-3}$-alkyl)-carboxy-$C_{1-3}$-alkylamino or N—($C_{1-3}$-alkyl)-$C_{1-3}$-alkoxycarbonyl-$C_{1-3}$-alkylamino group, whilst in the abovementioned groups the carbon atom in the α-position to the adjacent nitrogen atom may not be substituted, $R_3$ denotes a $C_{3-7}$-cycloalkyl group, a propargyl group, wherein the unsaturated part may not be linked directly to the nitrogen atom of the $R_2NR_3$ group, a phenyl group optionally substituted by a fluorine or chlorine atom, or by a methyl or methoxy group, a pyrazolyl, pyridazolyl or pyridinyl group optionally substituted by a methyl group or $R_2$ and $R_3$ together with the nitrogen atom between them denote a 5- to 7-membered cycloalkyleneimino group, optionally substituted by a carboxy or $C_{1-4}$-alkoxycarbonyl group, to which a phenyl ring may additionally be fused, the tautomers, the stereoisomers and the salts thereof. Compounds of formula (I), preparation of these compounds and their use as anticoagulants has been described in WO 98/37075.

In a further embodiment, the anticoagulant is a compound selected from (a) 2-[N-(4-amidinophenyl)-aminomethyl]-benzthiazole-5-carboxylic acid-N-phenyl-N-(2-carboxyethyl)-amide,
(b) 2-[N-(4-amidinophenyl)-N-methyl-aminomethyl]-benzthiazol-5-yl-carboxylic acid-N-phenyl-N-(2-hydroxycarbonylethyl)-amide,
(c) 1-Methyl-2-[N-(4-amidinophenyl)-aminomethyl]-benzimidazol-5-yl-carboxylic acid-N-phenyl-N-(2-hydroxycarbonylethyl)-amide,
(d) 1-Methyl-2-[N-(4-amidinophenyl)-aminomethyl]-benzimidazol-5-yl-carboxylic acid-N-phenyl-N-(3-hydroxycarbonylpropyl)-amide,
(e) 1-Methyl-2-[N-(4-amidinophenyl)-aminomethyl]-benzimidazol-5-yl-carboxylic acid-N-(2-pyridyl)-N-(hydroxycarbonylmethyl)-amide,
(f) 1-Methyl-2-[2-(2-amidinothiophen-5-yl)ethyl]-benzimidazol-5-yl-carboxylic acid-N-(2-pyridyl)-N-(2-hydroxycarbonylethyl)-amide,
(g) 1-Methyl-2-[N-(4-amidinophenyl)-aminomethyl]-benzimidazol-5-yl-carboxylic acid-N-(2-pyridyl)-N-(2-hydroxycarbonylethyl)-amide,
(h) 1-Methyl-2-[2-(4-amidinophenyl)ethyl]-benzimidazol-5-yl-carboxylic acid-N-(2-pyridyl)-N-(2-hydroxycarbonylethyl)-amide,
(i) 1-Methyl-2-[2-(4-amidinophenyl)ethyl]-benzimidazol-5-yl-carboxylic acid-N-phenyl-N-(2-hydroxycarbonylethyl)-amide,
(j) 1-Methyl-2-[2-(4-amidinophenyl)ethyl]-benzimidazol-5-yl-carboxylic acid-N-phenyl-N-[2-(1H-tetrazol-5-yl)ethyl]-amide,
(k) 1-Methyl-2-[N-(4-amidinophenyl)-aminomethyl]-benzimidazol-5-yl-carboxylic acid-N-phenyl-N-[2-(1H-tetrazol-5-yl)ethyl]-amide,
(l) 1-Methyl-2-[N-(4-amidinophenyl)-N-methyl-aminomethyl]-benzimidazol-5-yl-carboxylic acid-N-(2-pyridyl)-N-(2-hydroxycarbonylethyl)-amide,
(m) 1-Methyl-2-[N-(4-amidinophenyl)-N-methyl-aminomethyl]-benzimidazol-5-yl-carboxylic acid-N-(3-pyridyl)-N-(2-hydroxycarbonylethyl)-amide,
(n) 1-Methyl-2-[N-(4-amidinophenyl)-N-methyl-aminomethyl]-benzimidazol-5-yl-carboxylic acid-N-phenyl-N-(2-hydroxycarbonylethyl)-amide,
(o) 1-Methyl-2-[N-(4-amidinophenyl)-aminomethyl]-benzimidazol-5-yl-carboxylic acid-N-phenyl-N-[(N-hydroxycarbonylethyl-N-methyl)-2-aminoethyl]-amide,
(p) 1-Methyl-2-[N-(4-amidinophenyl)-aminomethyl]-benzimidazol-5-yl-carboxylic acid-N-(3-fluorophenyl)-N-(2-hydroxycarbonylethyl)-amide,
(q) 1-Methyl-2-[N-(4-amidinophenyl)-aminomethyl]-benzimidazol-5-yl-carboxylic acid-N-(4-fluorophenyl)-N-(2-hydroxycarbonylethyl)-amide,
(r) 1-Methyl-2-[N-(4-amidino-2-methoxy-phenyl)-aminomethyl]-benzimidazol-5-yl-carboxylic acid-N-phenyl-N-(2-hydroxycarbonylethyl)-amide,
(s) 1-Methyl-2-[N-(4-amidino-2-methoxy-phenyl)-aminomethyl]-benzimidazol-5-yl-carboxylic acid-N-(2-pyridyl)-N-(2-hydroxycarbonylethyl)-amide,
(t) 1-Methyl-2-[N-(4-amidinophenyl)aminomethyl]-indol-5-yl-carboxylic acid-N-phenyl-N-(2-methoxycarbonylethyl)-amide,
(u) 1-Methyl-2-[N-(4-amidinophenyl)aminomethyl]-thieno[2,3-d]imidazol-5-yl-carboxylic acid-N-phenyl-N-(2-hydroxycarbonylethyl)-amide,
(v) 1-Methyl-2-[N-(4-amidinophenyl)-aminomethyl]-benzimidazol-5-yl-carboxylic acid-N-phenyl-N-(2-hydroxycarbonylethyl)-amide,
(w) 1-Methyl-2-[N-(4-amidinophenyl)-aminomethyl]-benzimidazol-5-yl-carboxylic acid-N-(2-pyridyl)-N-(2-hydroxycarbonylethyl)-amide,
(x) 1-Methyl-2-[N-(4-amidino-2-methoxy-phenyl)-aminomethyl]-benzimidazol-5-yl-carboxylic acid-N-(2-pyridyl)-N-(2-hydroxycarbonylethyl)-amide,
(y) 1-Methyl-2-[N-[4-(N-n-hexyloxycarbonylamidino)phenyl]-aminomethyl]-benzimidazol-5-yl-carboxylic acid-N-(2-pyridyl)-N-(2-ethoxycarbonylethyl)-amide, and the tautomers, stereoisomers and the salts thereof, all of which have been described in WO 98/37075.

A preferred anticoagulant in the context of the present invention is dabigatran (CAS 211914-51-1, N-[2-(4-Amidinophenylaminomethyl)-1-methyl-1H-benzimidazol-5-ylcarbonyl]-N-(2-pyridyl)-beta-alanine) having the chemical formula (II):

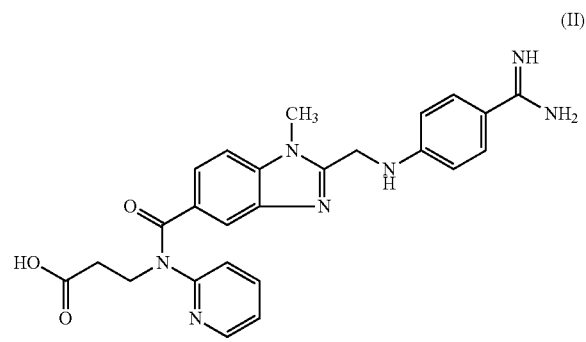 [SMILES: Cn1c(CNc2ccc(C(=N)N)cc2)nc2cc(C(=O)N(CCC(=O)O)c3ccccn3)ccc21]

Dabigatran is known from WO 98/37075, which discloses compounds with a thrombin-inhibiting effect and the effect of prolonging the thrombin time, under the name 1-Methyl-2-N-(4-amidinophenyl)-aminomethyl]-benzimidazol-5-yl-carboxylic acid-N-(2-pyridyl)-N-(2-hydroxycarbonylethyl)-amide. See also Hauel et al. J Med Chem 2002, 45 (9): 1757-66.

Dabigatran is applied as a prodrug of formula (III):

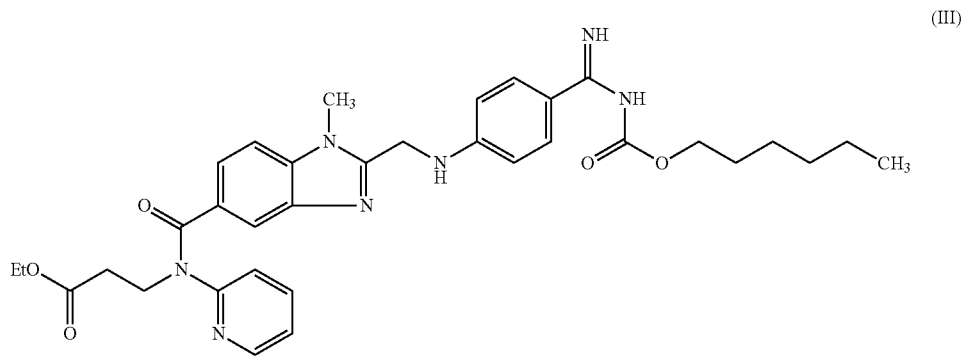 [SMILES: CCCCCCOC(=O)NC(=N)c1ccc(NCc2nc3cc(C(=O)N(CCC(=O)OCC)c4ccccn4)ccc3n2C)cc1]

The compound of formula III (named dabigatran etexilate, CAS 211915-06-9; ethyl 3-[(2-{[4-(hexyloxycarbonylamino-imino-methyl)-phenylamino]-methyl}-1-methyl-1H-benzimidazole-5-carbonyl)-pyridin-2-yl-amino]-propionate) is converted into the active compound (II) after entering the body. A preferred polymorph of dabigatran etexilate is dabigatran etexilate mesylate.

The main indications for dabigatran are the post-operative prevention of deep-vein thrombosis, the treatment of established deep vein thrombosis and the prevention of strokes in patients with atrial fibrillation (Eriksson et al., Lancet 2007, 370 (9591): 949-56; Schulman S et al, N Engl J Med 2009, 361 (24): 2342-52; Connolly S et al., N Engl J Med 2009, 361 (12): 1139-51; Wallentin et al., Lancet 2010, 376 (9745): 975-983).

In the human body, glucuronidation of the carboxylate moiety is the major human metabolic pathway of dabigatran (Ebner et al., Drug Metab. Dispos. 2010, 38(9):1567-75). It results in the formation of the 1-O-acylglucuronide (beta anomer). The 1-O-acylglucuronide, in addition to minor hydrolysis to the aglycon, may undergo nonenzymatic acyl migration in aqueous solution, resulting in the formation of the 2-O-, 3-O-, and 4-O-acylglucuronides. Experiments with the purified 1-O-acylglucuronide and its isomeric rearrangement products revealed equipotent prolongation of the activated partial thromboplastin time compared with dabigatran.

In another aspect of the invention, the antibody molecule binds both to dabigatran and dabigatran etexilate.

In another aspect of the invention, the antibody molecule binds both to dabigatran and O-acylglucuronides of dabigatran, in particular the 1-O-acylglucuronide of dabigatran.

In another aspect of the invention, the antibody molecule binds furthermore to the 2-O—, 3-O-, and 4-O-acylglucuronides of dabigatran.

In another aspect of the invention, the antibody molecule is capable of neutralizing the activity of dabigatran and O-acylglucuronides of dabigatran, in particular the 1-O-acylglucuronide of dabigatran.

Figure 5:
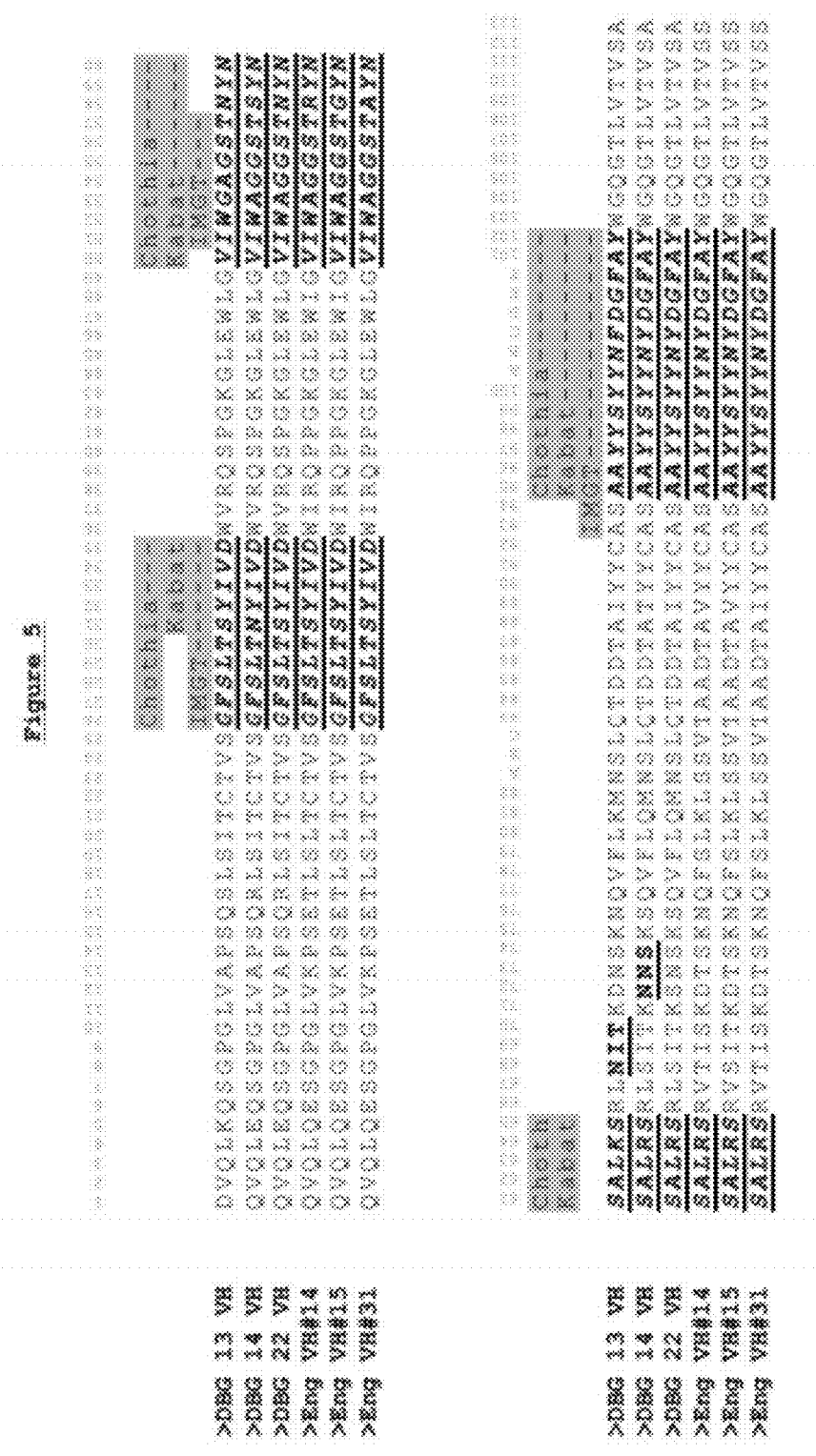
Figure 6:
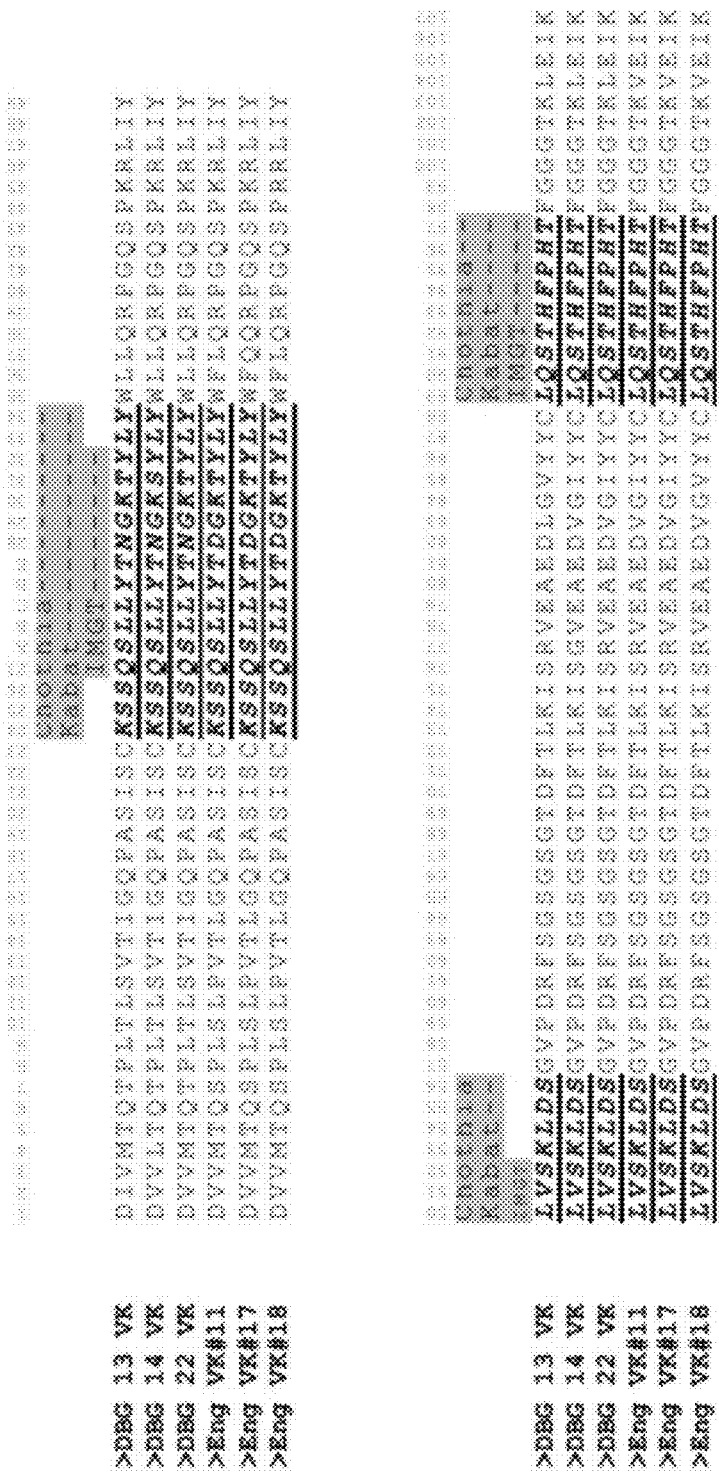
FIG. 6: Sequences of variable regions of anti-dabigatran antibody molecule light chains Sequences correspond to SEQ ID numbers in the Listing as follows: DBG 13 VK=SEQ ID NO:17; DBG 14 VK=SEQ ID NO:19; DBG 22 VK=SEQ ID NO:21; ENG VK#11=SEQ ID NO:23; ENG VK#17=SEQ ID NO:25; ENG VK#18=SEQ ID NO:27.

In another aspect of the invention, the antibody molecule has binding specificity for dabigatran and comprises CDR sequences as depicted in FIGS. 5 and 6.

In another aspect of the invention, the antibody molecule comprises heavy chain CDR sequences as depicted in FIG. 5, and light chain CDR sequences as depicted in FIG. 6.

In another aspect of the invention, the antibody molecule comprises a heavy chain variable domain sequence as depicted in FIG. 5, and a light chain variable domain sequence as depicted in FIG. 6.

In another aspect of the invention, the antibody molecule comprises a heavy chain variable domain sequence depicted with the designation DBG 13 VH in FIG. 5, and a light chain variable domain sequence as depicted with the designation DBG 13 VK in FIG. 6.

In another aspect of the invention, the antibody molecule comprises a heavy chain variable domain sequence depicted with the designation DBG 14 VH in FIG. 5, and a light chain variable domain sequence as depicted with the designation DBG 14 VK in FIG. 6.

In another aspect of the invention, the antibody molecule comprises a heavy chain variable domain sequence depicted with the designation DBG 22 VH in FIG. 5, and a light chain variable domain sequence as depicted with the designation DBG 22 VK in FIG. 6.

In another aspect of the invention, the antibody molecule comprises a heavy chain variable domain sequence depicted with the designation Eng VH# 14 in FIG. 5, and a light chain variable domain sequence as depicted with the designation Eng VK# 11 in FIG. 6.

In another aspect of the invention, the antibody molecule comprises a heavy chain variable domain sequence depicted with the designation Eng VH# 15 in FIG. 5, and a light chain variable domain sequence as depicted with the designation Eng VK# 17 in FIG. 6.

In another aspect of the invention, the antibody molecule comprises a heavy chain variable domain sequence depicted with the designation Eng VH# 15 in FIG. 5, and a light chain variable domain sequence as depicted with the designation Eng VK# 18 in FIG. 6.

In another aspect of the invention, the antibody molecule comprises a heavy chain variable domain sequence depicted with the designation Eng VH# 31 in FIG. 5, and a light chain variable domain sequence as depicted with the designation Eng VK# 18 in FIG. 6.

In another aspect of the invention, the antibody molecule has binding specificity for dabigatran and comprises a heavy chain variable domain with a CDR1 selected from the group consisting of SEQ ID NO: 1 and SEQ ID NO: 2, a CDR2 selected from the group consisting of SEQ ID NO: 3, SEQ ID NO: 4, SEQ ID NO: 5, SEQ ID NO: 6, SEQ ID NO: 7, and SEQ ID NO: 8, and a CDR3 selected from the group consisting of SEQ ID NO: 9 and SEQ ID NO: 10, and a light chain variable domain with a CDR1 selected from the group consisting of SEQ ID NO: 11, SEQ ID NO: 12, and SEQ ID NO: 13, a CDR2 of SEQ ID NO: 14, and a CDR3 of SEQ ID NO: 15.

In another aspect of the invention, the antibody molecule comprises a heavy chain variable domain with a CDR1 of SEQ ID NO: 1, a CDR2 selected from the group consisting of SEQ ID NO: 6, SEQ ID NO: 7, and SEQ ID NO: 8, a CDR3 of SEQ ID NO: 10, and a light chain variable domain with a CDR1 of SEQ ID NO: 13, a CDR2 of SEQ ID NO: 14, and a CDR3 of SEQ ID NO: 15.

In another aspect of the invention, the antibody molecule comprises a heavy chain variable domain with a CDR1 of SEQ ID NO: 1, a CDR2 of SEQ ID NO: 7, a CDR3 of SEQ ID NO: 10, and a light chain variable domain with a CDR1 of SEQ ID NO: 13, a CDR2 of SEQ ID NO: 14, and a CDR3 of SEQ ID NO: 15.

In another aspect of the invention, the antibody molecule comprises a heavy chain variable domain with a CDR1 of SEQ ID NO: 1, a CDR2 of SEQ ID NO: 5, a CDR3 of SEQ ID NO: 10, and a light chain variable domain with a CDR1 of SEQ ID NO: 11, a CDR2 of SEQ ID NO: 14, and a CDR3 of SEQ ID NO: 15.

In another aspect of the invention, the antibody molecule comprises a heavy chain variable domain selected from the group consisting of SEQ ID NOs: 16, 18, 20, 22, 24, and 26, and a light chain variable domain selected from the group consisting of SEQ ID Nos: 17, 19, 21, 23, 25, and 27.

In another aspect of the invention, the antibody molecule comprises a heavy chain variable domain of SEQ ID NO: 16, and a light chain variable domain of SEQ ID No: 17.

In another aspect of the invention, the antibody molecule comprises a heavy chain variable domain of SEQ ID NO: 18, and a light chain variable domain of SEQ ID No: 19.

In another aspect of the invention, the antibody molecule comprises a heavy chain variable domain of SEQ ID NO: 20, and a light chain variable domain of SEQ ID No: 21.

In another aspect of the invention, the antibody molecule comprises a heavy chain variable domain of SEQ ID NO: 22, and a light chain variable domain of SEQ ID No: 23.

In another aspect of the invention, the antibody molecule comprises a heavy chain variable domain of SEQ ID NO: 24, and a light chain variable domain of SEQ ID No: 25.

In another aspect of the invention, the antibody molecule comprises a heavy chain variable domain of SEQ ID NO: 24, and a light chain variable domain of SEQ ID No: 27.

In another aspect of the invention, the antibody molecule comprises a heavy chain variable domain of SEQ ID NO: 26, and a light chain variable domain of SEQ ID No: 27.

In another aspect of the invention, the antibody molecule is a scFv molecule. In this format, the variable domains disclosed herein may be fused to each other with a suitable linker peptide, e.g. selected from the group consisting of SEQ ID Nos: 28, 29, 30, or 31.

The construct may comprise these elements in the order, from N terminus to C terminus, (heavy chain variable domain)-(linker peptide)-(light chain variable domain), or (light chain variable domain)-(linker peptide)-(heavy chain variable domain).

In another aspect of the invention, the antibody molecule is a scFv molecule comprising SEQ ID NO: 32, or SEQ ID NO: 33. In another aspect of the invention, the antibody molecule is a scFv molecule consisting of SEQ ID NO: 32, or SEQ ID NO: 33.

Processes are known in the art which allow recombinant expression of nucleic acids encoding sFv constructs in host cells (like E. coli, Pichia pastoris, or mammalian cell lines, e.g. CHO or NS0), yielding functional scFv molecules (see e.g. Rippmann et al., Applied and Environmental Microbiology 1998, 64(12): 4862-4869; Yamawaki et al., J. Biosci. Bioeng. 2007, 104(5): 403-407; Sonoda et al., Protein Expr. Purif. 2010, 70(2): 248-253).

In particular, the scFv antibody molecules of the invention can be produced as follows. The constructs can be expressed in different E. coli strains like W3110, TG1, BL21, BL21 (DE3), HMS174, HM5174(DE3), MM294 under control of an inducible promoter. This promoter can be chosen from lacUV5, tac, T7, trp, trc, T5, araB. The cultivation media are preferably fully defined according to Wilms et al., 2001 (Wilms et al., Biotechnology and Bioengineering 2001, 73(2): 95-103), DeLisa et al., 1999 (DeLisa et al., Biotechnology and Bioengineering 1999, 65(1): 54-64) or equivalent. However, supplementation of the batch medium and/or feed medium with amino acids such as isoleucine, leucine, lysine, methionine, phenylalanine, threonine, tryptophan and valin or complex media components such as soy peptone or yeast extract may be beneficial. The process for fermentation is performed in a fed-batch mode. Conditions: Temperature 20-40° C., pH 5.5-7.5, DO is kept above 20%. After consumption of the initial carbon source the culture is fed with the feed media stated above (or equivalent). When a dry cell weight of 40 to 100 g/L is reached in the fermenter the culture is induced with an appropriate inducer corresponding to the used promoter system (e.g. IPTG, lactose, arabinose). The induction can either be performed as a pulsed full induction or as a partial induction by feeding the respective inducer into the fermenter over a prolonged time or a combination thereof. The production phase should last 4 hours at least. The cells are recovered by centrifugation in bowl centrifuges, tubular bowl centrifuges or disc stack centrifuges, the culture supernatant is discarded.

The E. coli cell mass is resuspended in 4- to 8-fold amount of lysis buffer (phosphate or Tris buffer, pH 7-8.5). Cell lysis is preferably performed by high pressure homogenization followed by recovery of the pellet by centrifugation in bowl, tubular bowl or disc stack centrifuges. Pellet containing scFv inclusion bodies is washed 2-3 times with 20 mM Tris, 150 mM NaCl, 5 mM EDTA, 2 M Urea, 0.5% Triton X-100, pH 8.0 followed by two wash steps using 20 mM Tris, 150 mM NaCl, 5 mM EDTA, pH 8.0. scFv inclusion bodies are finally recovered by centrifugation in bowl, tubular bowl or disc stack centrifuges. Solubilisation of scFv inclusion bodies can be performed in 100 mM Glycine/NaOH, 5 mM EDTA, 20 mM dithiothreitol, pH 9.5-10.5 containing chaotropic agents such as 6 M Guanidine-HCl or 8-10 mM Urea. After incubation for 30-60 minutes solution is centrifuged and supernatant containing the target protein recovered for subsequent refolding. Refolding is preferably performed in fed batch mode by diluting the protein solution 1:10-1:50 in refolding buffer to a final protein concentration of 0.1-0.5 mg/ml. Refolding buffer can contain 50-100 mM Tris and/or 50-100 mM Glycine, 50-150 mM NaCl, 1-3 M urea, 0.5-1 M arginine, 2-6 mM of redox system such as e.g. cytein/cystine or oxidized/reduced glutathione, pH 9.5-10.5. After incubation for 24-72 h at 4° C. refolding solution is optionally filtrated using a 0.22 µm filter, diluted and pH adjusted to pH 7.0-8.0. Protein is separated via cation exchange chromatography in binding mode (e.g. Toyopearl GigaCap S-650M, SP Sepharose FF or S HyperCel™) at pH 7.0-8.5. Elution is performed by a linear increasing NaCl gradient. Fractions containing the target protein are pooled and subsequently separated on anion exchange column in non-binding mode (e.g. Toyopearl GigaCap Q-650M, Q-Sepharose FF, Q HyperCel™) followed by a cation exchange polishing step (eg. SP Sepharose HP). Fractions containing the target protein with a purity level of minimally 90% are pooled and formulated by diafiltration or size exclusion chromatography in PBS. Identity and product quality of the produced scFv molecule are analysed by reducing SDS-PAGE where the scFv can be detected in one major band of approx. 26 kDa. Further assays for characterization of the scFv include mass spectrometry, RP-HPLC and SE-HPLC.

In another aspect of the invention, the antibody molecule is an immunoglobulin, preferably an immunoglobulin of type IgG1, or effector function knock-out thereof, or IgG4. In another aspect of the invention, the antibody molecule is an immunoglobulin having a heavy chain comprising SEQ ID NO: 34, SEQ ID NO: 40, or SEQ ID NO: 42, and a light chain comprising SEQ ID NO: 35 or SEQ ID NO: 43.

In another aspect of the invention, the antibody molecule is an immunoglobulin having a heavy chain comprising SEQ ID NO: 34, and a light chain comprising SEQ ID NO: 35, or a heavy chain comprising SEQ ID NO: 40, and an light chain comprising SEQ ID NO: 35. In another aspect of the invention, the antibody molecule is an immunoglobulin having a heavy chain comprising or SEQ ID NO: 42, and a light chain comprising SEQ ID NO: 43.

In another aspect of the invention, the antibody molecule is an immunoglobulin having a heavy chain consisting of SEQ ID NO: 34, and a light chain consisting of SEQ ID NO: 35, or a heavy chain consisting of SEQ ID NO: 40, and an light chain consisting of SEQ ID NO: 35. In another aspect of the invention, the antibody molecule is an immunoglobulin having a heavy chain consisting of or SEQ ID NO: 42, and a light chain consisting of SEQ ID NO: 43.

In another aspect of the invention, the antibody molecule is a Fab molecule. In that format, the variable domains disclosed above may each be fused to an immunoglobulin constant domain, preferably of human origin. Thus, the heavy chain variable domain may be fused to a CH, domain (a so-called Fd fragment), and the light chain variable domain may be fused to a CL domain.

In another aspect of the invention, the antibody molecule is a Fab molecule having a Fd fragment comprising SEQ ID NO: 36 or SEQ ID NO: 38, and a light chain comprising SEQ ID NO: 37 or SEQ ID NO: 39. In another aspect of the invention, the antibody molecule is a Fab molecule having a Fd fragment comprising SEQ ID NO: 36, and a light chain comprising SEQ ID NO: 37. In another aspect of the invention, the antibody molecule is a Fab molecule having a Fd fragment comprising SEQ ID NO: 38, and a light chain comprising SEQ ID NO: 39. In another aspect of the invention, the antibody molecule is a Fab molecule having a Fd fragment comprising SEQ ID NO: 41, and a light chain comprising SEQ ID NO: 37. In another aspect of the invention, the antibody molecule is a Fab molecule having a Fd fragment consisting of SEQ ID NO: 36, and a light chain consisting of SEQ ID NO: 37. In another aspect of the invention, the antibody molecule is a Fab molecule having a Fd fragment consisting of SEQ ID NO: 38, and a light chain consisting of SEQ ID NO: 39. In another aspect of the invention, the antibody molecule is a Fab molecule having a Fd fragment consisting of SEQ ID NO: 41, and a light chain consisting of SEQ ID NO: 37.

Nucleic acids encoding Fab constructs may be used to express such heavy and light chains in host cells, like *E. coli, Pichia pastoris*, or mammalian cell lines (e.g. CHO, or NS0). Processes are known in the art which allow proper folding, association, and disulfide bonding of these chains into functional Fab molecules comprising a Fd fragment and a light chain (Burtet et al., J. Biochem. 2007, 142(6), 665-669; Ning et al., Biochem. Mol. Biol. 2005, 38: 204-299; Quintero-Hernandez et al., Mol. Immunol. 2007, 44: 1307-1315; Willems et al. J. Chromatogr. B. Analyt. Technol. Biomed. Life Sci. 2003; 786:161-176).

In particular, Fab molecules of the invention can be produced in CHO cells as follows. CHO-DG44 cells (Urlaub, G., Kas, E., Carothers, A. M., and Chasin, L. A. (1983). Deletion of the diploid dihydrofolate reductase locus from cultured mammalian cells. Cell 33, 405-412) growing in suspension in serum-free medium are transfected with expression constructs encoding heavy and light chain of the Fab molecule using Lipofectamine™ and Plus™ reagent (Invitrogen) according to the manufacturer's instructions. After 48 hours, the cells are subjected to selection in medium containing 200 µg/mL of the antibiotic G418 and without hypoxanthine and thymidine to generate stably transfected cell populations. These stable transfectants are subsequently subjected to gene amplification by adding methotrexate (MTX) in increasing concentrations (up to 100 or 400 nM) into the culture medium. Once the cells have adapted, they are subjected to fed-batch fermentations over 10 to 11 days to produce Fab protein material.

Suspension cultures of CHO-DG44 cells and stable transfectants thereof are incubated in chemically defined, serum-free cultivation media. Seed stock cultures are sub-cultivated every 2-3 days with seeding densities of $3 \times 10^5$-$2 \times 10^5$ cells/mL respectively. Cells are grown in shake flasks in Multitron HT incubators (Infors) at 5% CO2, 37° C. and 120 rpm. For fed-batch experiments, cells are seeded at $3 \times 10^5$ cells/mL into shake flasks in BI-proprietary production medium without antibiotics or MTX. The cultures are agitated at 120 rpm in 37° C. and 5% CO2 which is later reduced to 2% as cell numbers increase. Culture parameters including cell count, viability, pH, glucose and lactate concentrations are determined daily and pH is adjusted to pH 7.0 using carbonate as needed. BI-proprietary feed solution is added every 24 hrs. Samples from the supernatant are taken at different time points to determine the Fab product concentration by ELISA. After 10 to 11 days, the cell culture fluid is harvested by centrifugation and transferred to the purification labs.

The Fab molecule is purified from the supernatant of the fed-batch cultures by means of chromatography and filtration. As primary capture step affinity chromatography, e.g. Protein G or Protein L, are applied. Alternatively, in case of low binding affinities and capacities, the Fab is captured by cation exchange chromatography (CEX) exploiting the pI of the molecule. Host cell proteins and contaminants, e.g. DNA or viruses, are removed by additional orthogonal purification steps.

Identity and product quality of the produced Fab molecule are analysed by electrophoretic methods, e.g. SDS-PAGE, by which Fab can be detected as one major band of approx. 50 kDa. Further assays for characterization of the Fab product include mass spectrometry, isoelectric focusing and size exclusion chromatography. Binding activity is followed by BIAcore analysis.

Quantification of Fab or full-length IgG molecules in the supernatant of the cell cultures is performed via sandwich enzyme linked immunosorbent assay (ELISA). The full-length IgG can be detected using antibodies raised against human-Fc fragment (Jackson Immuno Research Laboratories) and human kappa light chain (peroxidase-conjugated, Sigma). The Fab fragment is immobilized by goat polyclonal anti-Human IgG (H and L, Novus) and detected by sheep polyclonal antibodies raised against human IgG (peroxidase-conjugated, The Binding Site).

Fab molecules can also be generated from full-length antibody molecules by enzymatic cleavage. The advantage of this approach is that platform processes for robust and efficient fermentation and purification are applicable which are amenable for up-scaling and high yields at the desired product quality. For purification affinity chromatography using a recombinant Protein A resin can be used as primary capture step which usually results in high purities.

For this purpose, the heavy chain encoding Fab sequences are fused to the Fc-region of a human IgG antibody molecule. The resulting expression constructs are then transfected into CHO-DG44 cells growing in suspension in serum-free medium using lipofection. After 48 hours, the cells are subjected to selection in medium containing 200 μg/mL of the antibiotic G418 and without hypoxanthine and thymidine to generate stably transfected cell populations. These stable transfectants are subsequently subjected to gene amplification by adding methotrexate (MTX) in increasing concentrations (up to 100 or 400 nM) into the culture medium. Once the cells have adapted, they are subjected to fed-batch fermentations over 10 to 11 days to produce IgG protein material. The IgG protein is purified from the culture supernatant by using recombinant Protein A-affinity chromatography. To obtain the desired neutralizing Fab fragment the full-length IgG is then incubated in the presence of papain which cleaves the IgG within the hinge region, thereby releasing two Fab fragments and the Fc-moiety. A Fab molecule comprising a Fd chain of SEQ ID NO: 41 is an example of a Fab molecule obtained by papain digestion of a full-length IgG protein.

The Fab molecule is isolated by affinity chromatography, e.g. Protein G or Protein L. Alternatively, in case of low binding affinities and capacities, the Fab is captured by cation exchange chromatography (CEX) exploiting the pl of the molecule. Host cell proteins and contaminants, e.g. Papain, DNA or viruses, are removed by additional orthogonal purification steps.

In another aspect of the invention, the antibody molecule is an amino acid sequence variant of an antibody molecule as described herein.

Amino acid sequence variants of antibodies can be prepared by introducing appropriate nucleotide changes into the antibody DNA, or by peptide synthesis. Such variants include, for example, deletions from, and/or insertions into and/or substitutions of, residues within the amino acid sequences of the antibodies of the examples herein. Any combination of deletions, insertions, and substitutions is made to arrive at the final construct, provided that the final construct possesses the desired characteristics. The amino acid changes also may alter post-translational processes of the humanized or variant antibody, such as changing the number or position of glycosylation sites.

A useful method for identification of certain residues or regions of the antibody that are preferred locations for mutagenesis is called "alanine scanning mutagenesis," as described by Cunningham and Wells (Science, 244:1081-1085 (1989)). Here, a residue or group of target residues are identified (e.g., charged residues such as arg, asp, his, lys, and glu) and replaced by a neutral or negatively charged amino acid (typically alanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody fused to an epitope tag. Other insertional variants of the antibody molecule include a fusion to the N- or C-terminus of the antibody of an enzyme or a polypeptide which increases the serum half-life of the antibody.

Another type of variant is an amino acid substitution variant. These variants have at least one amino acid residue in the antibody molecule removed and a different residue inserted in its place. The sites of greatest interest for substitutional mutagenesis include the hypervariable regions, but FR alterations are also contemplated. Conservative substitutions are shown in the Table below under the heading of "preferred substitutions". If such substitutions result in a change in biological activity, then more substantial changes, denominated "exemplary substitutions", or as further described below in reference to amino acid classes, may be introduced and the products screened.

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |
| Thr (T) | ser | ser |
| Trp (W) | tyr; phe | tyr |
| Tyr (Y) | phe; trp; thr; ser | phe |
| Val (V) | leu; ile; met; phe ala; norleucine; | leu |

In protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class.

Any cysteine residue not involved in maintaining the proper conformation of the humanized or variant antibody also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody to improve its stability (particularly where the antibody is an antibody fragment such as an Fv fragment).

A type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human Dabigatran. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By "altering" is meant deleting one or more carbohydrate moieties found in the antibody, and/or adding one or more glycosylation sites that are not present in the antibody.

In some embodiments, it may be desirable to modify the antibodies of the invention to add glycosylations sites. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. Thus, in order to glycosylate a given protein, e.g., an antibody, the amino acid sequence of the protein is engineered to contain one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of an antibody molecule as described herein. As outlined above, the antigen of the antibody molecule of the invention is an anticoagulant. The antigen is used to generate the antibody molecule, either by immunization of an animal, or by selecting antibody sequences from sequence libraries, as with phage display methods.

Immunization protocols for animals are well-known in the art. To achieve a proper immune response, it may be necessary to combine the antigen with an adjuvant, like aluminium phosphate, aluminium hydroxide, squalene, or Freund's complete/incomplete adjuvant. The antigens in the context of the present invention, like dabigatran, are mostly comparably small organic molecules, which sometimes do not stimulate antibody formation upon administration to an animal. It may therefore be necessary to attach the antigen to a macromolecule, as a hapten.

In a further aspect, the present invention relates to an antibody molecule as described above for use in medicine.

In a further aspect, the present invention relates to a pharmaceutical composition comprising an antibody molecule as described before, and a pharmaceutical carrier.

To be used in therapy, the antibody molecule is included into pharmaceutical compositions appropriate to facilitate administration to animals or humans. Typical formulations of the antibody molecule can be prepared by mixing the antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed. They include buffer systems such as phosphate, citrate, acetate and other anorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. Also organic solvents can be contained in the antibody formulation such as ethanol or isopropanol. The excipients may also have a release-modifying or absorption-modifying function.

In one aspect, the pharmaceutical composition comprises the antibody molecule in an aqueous, buffered solution at a concentration of 10-20 mg/ml, or a lyophilisate made from such a solution.

The preferred mode of application is parenteral, by infusion or injection (intraveneous, intramuscular, subcutaneous, intraperitoneal, intradermal), but other modes of application such as by inhalation, transdermal, intranasal, buccal, oral, may also be applicable.

In a further aspect, the present invention relates to an antibody molecule as described above for use in the therapy or prevention of side effects of anticoagulant therapy, in particular bleeding events.

In a further aspect, the present invention relates to an antibody molecule as described above for use in the reversal of an overdosing of an anticoagulant, in particular dabigatran or dabigatran exetilate.

In a further aspect, the present invention relates to an antibody molecule as described above for use as an antidote of an anticoagulant, in particular dabigatran or dabigatran exetilate.

In a further aspect, the present invention relates to a method of treatment or prevention of side effects of anticoagulant therapy, comprising administering an effective amount of an antibody molecule as described above to a patient in need thereof.

In a further aspect, the present invention relates to a method of treatment of an overdosing event in anticoagulant therapy, comprising administering an effective amount of an antibody molecule as described above to a patient in need thereof.

The "therapeutically effective amount" of the antibody to be administered is the minimum amount necessary to prevent, ameliorate, or treat the side effects of anticoagulant therapy, in particular the minimum amount which is effective to stop bleeding. This can be achieved with stoichiometric amounts of antibody molecule.

Dabigatran, for example, may achieve a plasma concentration in the magnitude of 200 nM when given at the recommended dose. When a monovalent antibody molecule with a molecular weight of ca. 50 kD is used, neutralization may be achieved for example at a dose of about 1 mg/kg, when given intravenously as a bolus. In another embodiment, the dose of a Fab molecule applied to a human patient may be 50-1000 mg per application, for example 100, 200, 500, 750, or 1000 mg. Depending on the situation, e.g. when dabigatran has been overdosed in a patient, it may be adequate to apply an even higher dose, e.g. 1250, 1500, 1750 or 2000 mg per application. The appropriate dose may be different, depending on the type and dose of anticoagulant administered; the time elapsed since such administration, the nature of the antigen molecule, the condition of the patient, and other factors. The skilled expert knows methods to establish doses which are both therapeutically effective and safe.

In a further aspect, the present invention relates to an antibody molecule with binding affinity to dabigatran and/or dabigatran etexilate. Preferably, the antibody molecule binds to the dabigatran and/or dabigatran etexilate with an affinity, as determined e.g. by surface plasmon resonance analysis (Malmqvist M., "Surface plasmon resonance for detection and measurement of antibody-antigen affinity and kinetics. "Curr Opin Immunol. 1993 April; 5(2):282-6) or kinetic exclusion assay (KinExA) technology (Darling, R. J., and Brault P.-A., "Kinetic exclusion assay technology: Characterization of Molecular Interactions." ASSAY and Drug Development Technologies. 2004, December 2(6): 647-657), with a $K_D$ value ranging from 0.1 pM to 100 µM, preferably 1 pM to 100 µM, more preferably 1 pM to 1 µM.

The antibody molecules of the invention can also be used for analytical and diagnostic procedures, for example to determine antigen concentration in samples such as plasma, serum, or other body fluids. For example, the antigen molecules may be used in an enzyme-linked immunoadsorbent assay (ELISA), like those described in the examples. Thus, in a further aspect, the present invention relates to analytical and diagnostic kits comprising antibody molecules a described herein, and to respective analytical and diagnostic methods.

In a further aspect, the present invention relates to a method of manufacturing an antibody molecule of any one of the preceding claims, comprising
 (a) providing a host cell comprising one or more nucleic acids encoding said antibody molecule in functional association with an expression control sequence,
 (b) cultivating said host cell, and
 (c) recovering the antibody molecule from the cell culture.

The invention further provides an article of manufacture and kit containing materials useful for neutralization of oral anticoagulants, particularly direct thrombin inhibitors. The article of manufacture comprises a container with a label. Suitable containers include, for example, bottles, vials, and test tubes. The containers may be formed from a variety of materials such as glass, metal, plastic or combinations thereof. The container holds a pharmaceutical composition comprising the antibody described herein or dabigatran, dabigatran etexilate, a prodrug of dabigatran or a pharmaceutically acceptable salt thereof. The active agent in the pharmaceutical composition is the particular antibody or dabigatran, dabigatran etexilate, a prodrug of dabigatran or a pharmaceutically acceptable salt thereof. The label on the container of the antibody indicates that the pharmaceutical composition is used for neutralizing or partially neutralizing dabigatran, dabigatran etexilate, a prodrug of dabigatran or a pharmaceutically acceptable salt thereof in vivo.

The kit of the invention comprises one or more of the containers described above. It may further include other materials desirable from a commercial and user standpoint, including other buffers, diluents, filters, needles, syringes, and package inserts with instructions for use.

In one embodiment of the invention, the kit comprises an antibody of any one the antibodies described herein or a pharmaceutical composition thereof. For example, the kit may comprise (1) any one the antibodies described herein or a pharmaceutical composition thereof, (2) a container and (3) a label.

In another embodiment, the kit comprises an antibody of any one the antibodies described herein or a pharmaceutical composition thereof, and dabigatran, dabigatran etexilate, a prodrug of dabigatran or a pharmaceutically acceptable salt thereof. The form of dabigatran, dabigatran etexilate, a prodrug of dabigatran or a pharmaceutically acceptable salt thereof may be in the form of a solid, liquid or gel. In a preferred embodiment, the pharmaceutically acceptable salt of dabigatran etexilate is a mesylate salt. In yet another preferred embodiment, the strength per dosage unit of the dabigatran, dabigatran etexilate, prodrug of dabigatran or pharmaceutically acceptable salt thereof is between about 50 mg and about 400 mg, about 75 mg and about 300 mg, about 75 mg and 150 mg, or about 110 mg and about 150 mg, given once-a-day (QD) or twice-a-day (BID). For example, the kit may comprise (1) any one the antibodies described herein or a pharmaceutical composition thereof, (2) a pharmaceutical composition of dabigatran, dabigatran etexilate, a prodrug of dabigatran or a pharmaceutically acceptable salt thereof, (3) a container and (4) a label.

In an alternate embodiment, the kit comprises (1) a first pharmaceutical composition comprising dabigatran, dabigatran etexilate, a prodrug of dabigatran or a pharmaceutically acceptable salt thereof, (2) a second pharmaceutical composition comprising any one the antibodies described herein or combination thereof, (3) instructions for separate administration of said first and second pharmaceutical compositions to a patient, wherein said first and second pharmaceutical compositions are contained in separate containers and said second pharmaceutical composition is administered to a patient requiring neutralization or partial neutralization of dabigatran or 1-O-acylglucuronide of dabigatran. The invention also provides a diagnostic method to neutralize or partially neutralize dabigatran or 1-O-acylglucuronide of dabigatran in a patient being treated with dabigatran, dabigatran etexilate, a prodrug of dabigatran or a pharmaceutically acceptable salt thereof, comprising administering any one of the antibodies described herein, a combination thereof or a pharmaceutical composition thereof. Specifically, the invention provides a method for neutralizing or partially neutralizing dabigatran or 1-O-acylglucuronide of dabigatran in a patient comprising the steps of (a) confirming that a patient was being treated with dabigatran, dabigatran etexilate, a prodrug of dabigatran or a pharmaceutically acceptable salt thereof, and the amount that was taken by the patient; (b) neutralizing dabigatran or 1-O-acylglucuronide with any one of the antibodies described herein or combination thereof prior to performing a clotting or coagulation test or assay wherein dabigatran or the 1-O-acylglucuronide of dabigatran would interfere with the accurate read out of the test or assay results; (c) performing the clotting or coagulation test or assay on a sample taken from the patient to determine the level of clot formation without dabigatran or 1-O-acylglucuronide of dabigatran present; and (d) adjusting an amount of dabigatran, dabigatran etexilate, a prodrug of dabigatran or a pharmaceutically acceptable salt thereof administered to the patient in order to achieve the appropriate balance between clot formation and degradation in a patient. The molar ratio of antibody to dabigatran or 1-O-acylglucuronide of dabigatran is in the molar ratio of between 0.1 and 100, preferably between 0.1 and 10. The accurate read out of the test or assay result may be an accurate read out of fibrinogen levels, activated protein C resistance or related tests.

EXAMPLES

I. Production of Polyclonal Anti-Dabigatran Antibodies

For the production of polyclonal anti-dabigatran antibodies, 3 different immunogens were produced with two different haptens and different molar input ratios of the hapten and the carrier protein (BSA).

For the screening, an enzyme horseradish peroxidase (HRP)-conjugate was produced and an enzyme-immunosorbent assay (ELISA) developed.

Further purification of the polyclonal antibodies was performed by affinity chromatography on protein A sepharose FF.

1. Materials and Methods
Test Compound (Dabigatran)

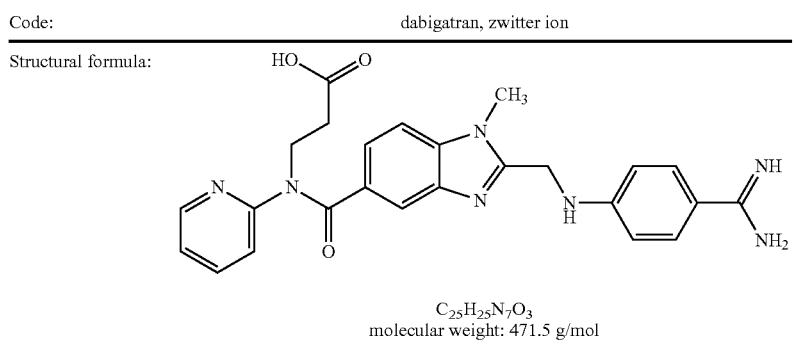

1.1 Hapten Used for Synthesis of Immunogen and Tracer

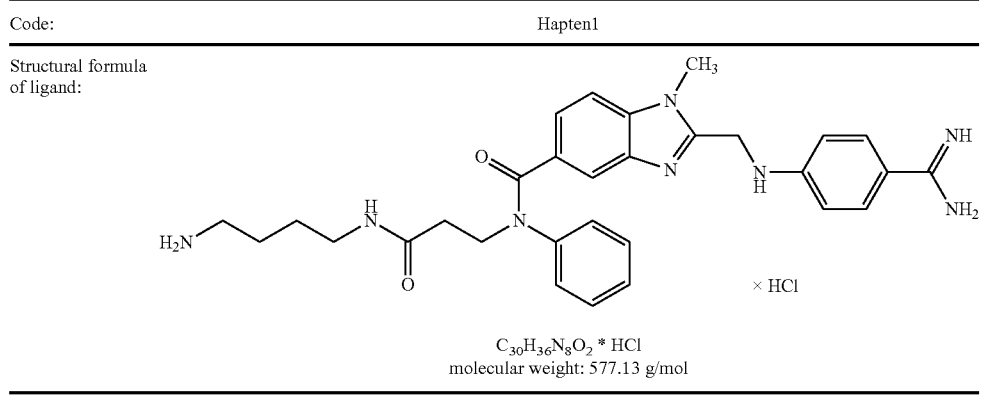

| Code: | Hapten2 |
|---|---|

Structural formula of ligand:

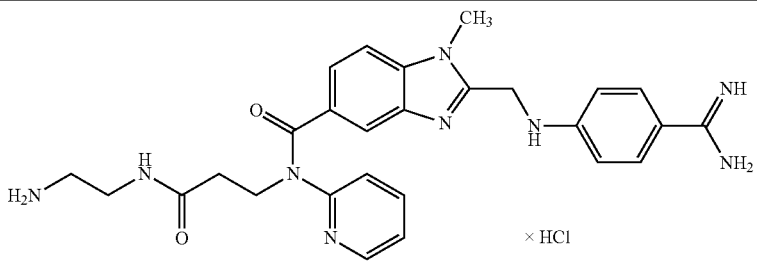

$C_{27}H_{31}N_9O_2$ * HCl
molecular weight: 550.07 g/mol

1.2 Synthesis of Haptens

The haptens Hapten1 and Hapten2 were synthesized as follows:

Hapten1 2-[(4-Carbamimidoyl-phenylamino)-methyl]-1-methyl-1H-benzoimidazole-5-carboxylic acid [2-(4-amino-butylcarbamoyl)-ethyl]phenyl-amide

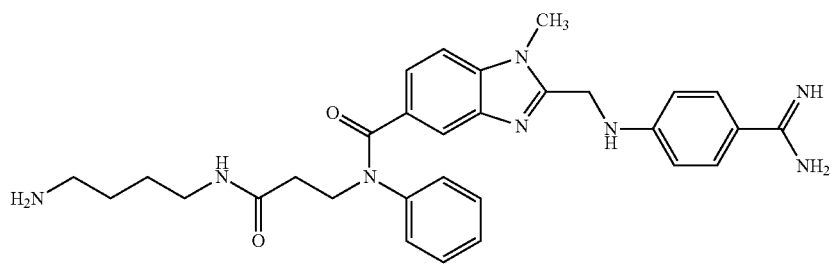 [SMILES: Cn1c(CNc2ccc(C(=N)N)cc2)nc2cc(C(=O)N(CCC(=O)NCCCCN)c3ccccc3)ccc21]

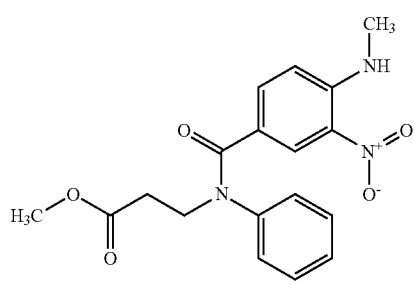 [SMILES: CNc1ccc(C(=O)N(CCC(=O)OC)c2ccccc2)cc1[N+](=O)[O-]]

1a 3-[(4-Methylamino-3-nitro-benzoyl)-phenyl-amino]propionic acid methyl ester

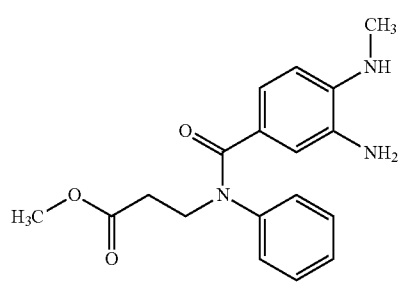

1b 3-[(3-Amino-4-methylamino-benzoyl)-phenyl-amino]propionic acid methyl ester

To a solution of 4-methylamino-3-nitro-benzoic acid chloride (23.3 mmol) and 3-phenylamino-propionic acid methyl ester (23.3 mmol) in 80 mL dry tetrahydrofuran (THF) triethylamine (50.2 mmol) was added dropwise under stirring at room temperature. After three hours the reaction mixture was evaporated to dryness, the remaining solid triturated with water and the solid product isolated through filtration.

Yield: 99%
$C_{18}H_{19}N_3O_5$ (357.36)
TLC (silica gel; Dichloromethane/ethanol 19:1): $R_f$=0.48

The nitro group of product 1a was reduced by hydrogenation at room temperature in ethanol with Pd (10% on charcoal) as catalyst.

Yield: 99%
$C_{18}H_{21}N_3O_3$ (327.38)
TLC (silica gel; Dichloromethane/ethanol 9:1): $R_f$=0.23
Mass spectrum (ESI): [M+H]$^+$=328

1c 3-({3-[2-(4-Cyano-phenylamino)-acetylamino]-4-methylamino-benzoyl}-phenylamino)-propionic acid methyl ester

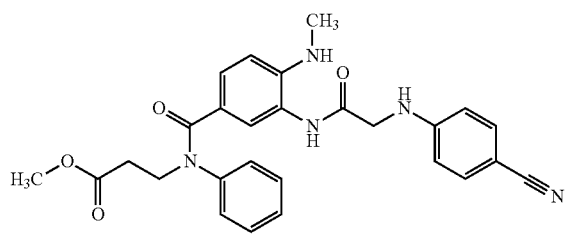 [SMILES: CNc1ccc(C(=O)N(CCC(=O)OC)c2ccccc2)cc1NC(=O)CNc1ccc(C#N)cc1]

The product of 1b (23.2 mmol) and N-(4-cyano-phenyl)-glycine (23.2 mmol) were coupled with CDI (23.2 mmol) in dry THF at room temperature. After completion of the reaction the mixture was evaporated to dryness and the crude product was used without further purification.

Yield: 97%
$C_{27}H_{27}N_5O_4$ (485.54)
Mass spectrum (ESI): $[M+H]^+=486$

1d 3-({2-[(4-Cyano-phenylamino)-methyl]-1-methyl-1H-benzoimidazole-5-carbonyl}-phenylamino)-propionic acid methyl ester

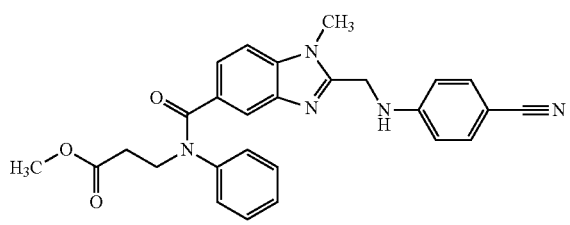 [SMILES: COC(=O)CCN(C(=O)c1ccc2c(c1)nc(CNc1ccc(C#N)cc1)n2C)c1ccccc1]

A solution of the product of 1c (22.6 mmol) in 100 mL concentrated acetic acid was heated to reflux for one hour. The solution was then evaporated to dryness, the remaining solid triturated with water and under stirring the pH was adjusted to about 8-9. The crude product was isolated through extraction with ethyl acetate and purified by chromatography on silica gel (eluent: dichloromethane/ethanol 1:1).

Yield: 58%
$C_{27}H_{25}N_5O_3$ (467.52)
TLC (silica gel; Dichloromethane/ethanol 9:1): $R_f=0.71$
Mass spectrum (ESI): $[M+H]^+=468$

1e 3-({2-[(4-Cyano-phenylamino)-methyl]-1-methyl-1H-benzoimidazole-5-carbonyl}-phenylamino)-propionic acid

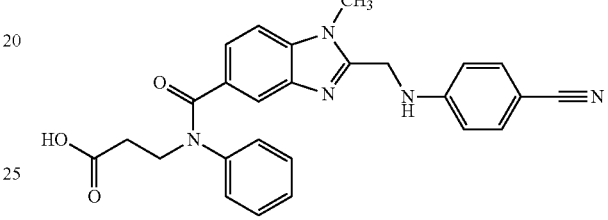

To a solution of the product of 1d (13.0 mmol) in 100 mL methanol sodium hydroxide (20.0 mmol) was added. The mixture was stirred for 2.5 hours at 40° C. and then evaporated to dryness. The remaining solid was stirred with 100 mL water and the pH was adjusted to about 6 with concentrated acetic acid. The precipitated product was isolated by filtration, washed with water and dried at 60° C.

Yield: 88%
$C_{26}H_{23}N_5O_3$ (453.49)
TLC (silica gel; Dichloromethane/ethanol 9:1): $R_f=0.33$
Mass spectrum (ESI): $[M+H]^+=454$

1f {4-[3-({2-[(4-Cyano-phenylamino)-methyl]-1-methyl-1H-benzoimidazole-5-carbonyl}-phenylamino)-propionylamino]-butyl}-carbamic acid tert-butyl ester

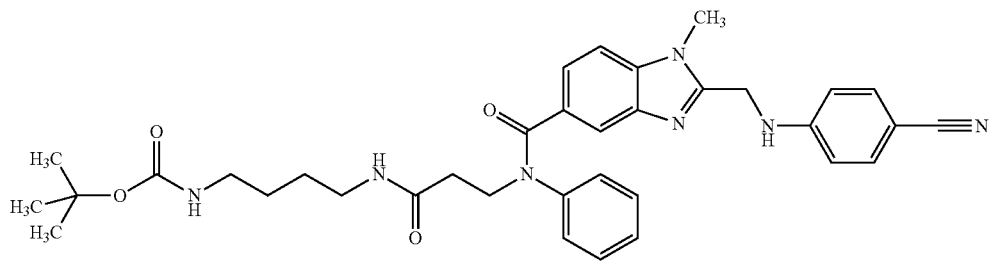 [SMILES: Cn1c(CNc2ccc(C#N)cc2)nc2cc(C(=O)N(CCC(=O)NCCCCNC(=O)OC(C)(C)C)c3ccccc3)ccc21]

A solution of the product of 1e (5.23 mmol), 2-(1H-benzotriazole-1-yl)-1,1,3,3-tetramethyluronium tetrafluoroborate (TBTU, 5.23 mmol) and N-methyl-morpholin (5.23 mmol) in 20 mL DMF was stirred at room temperature for 30 minutes. Then (4-aminobutyl)-carbamic acid tert-butyl ester (5.23 mmol) was added and the mixture stirred at room temperature for another 24 hours. The mixture was then diluted with water (100 mL) and the product was isolated through extraction with ethyl acetate.
Yield: 92%
$C_{35}H_{41}N_7O_4$ (623.75)
TLC (silica gel; Dichloromethane/ethanol 9:1): $R_f$=0.51

1 g. 2-[(4-Carbamimidoyl-phenylamino)-methyl]-1-methyl-1H-benzoimidazole-5-carboxylic acid [2-(4-amino-butylcarbamoyl)-ethyl]phenyl-amide

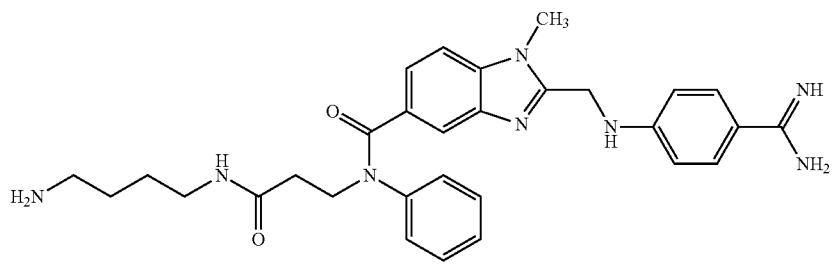 [SMILES: Cn1c(CNc2ccc(C(=N)N)cc2)nc2cc(C(=O)N(CCC(=O)NCCCCN)c3ccccc3)ccc21]

The product of if (4.81 mmol) was dissolved in a saturated solution of HCl in ethanol (250 mL), the mixture stirred at room temperature over night and then evaporated to dryness at 30° C. The remaining raw material was dissolved in 200 mL dry ethanol, then ammonium carbonate (48.1 mmol) was added and the mixture stirred at room temperature over night. After evaporation of the solvent the remaining raw material was triturated with ca. 5 mL ethanol, the undissolved material separated by filtration and the solvent evaporated at 30° C. The product was then dissolved in 30 mL water, the solution stirred with ca.2g charcoal, filtered and evaporated to dryness.
Yield: 90%
$C_{30}H_{36}N_8O_2$ (540.67)
TLC (reversed phase RP-8; methanol/5% aqueous NaCl solution 9:1): $R_f$=0.79
Mass spectrum (ESI): $[M+H]^+$=541
$[M+Cl]^-$=575/7

Hapten2 2-[(4-Carbamimidoyl-phenylamino)-methyl]-1-methyl-1H-benzoimidazole-5-carboxylic acid [2-(2-amino-ethylcarbamoyl)-ethyl]pyridin-2-yl-amide

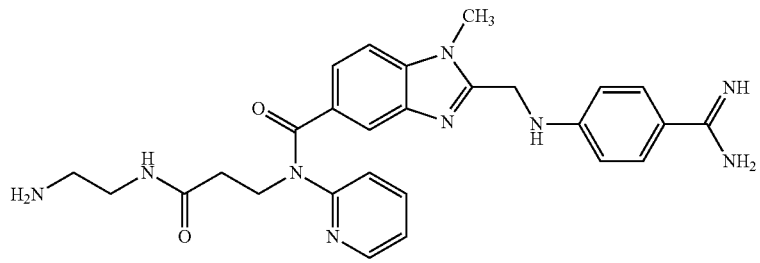 [SMILES: Cn1c(CNc2ccc(C(=N)N)cc2)nc2cc(C(=O)N(CCC(=O)NCCN)c3ccccn3)ccc21]

2a 3-({2-[(4-Cyano-phenylamino)-methyl]-1-methyl-1H-benzoimidazole-5-carbonyl}-pyridin-2-yl-amino)-propionic acid

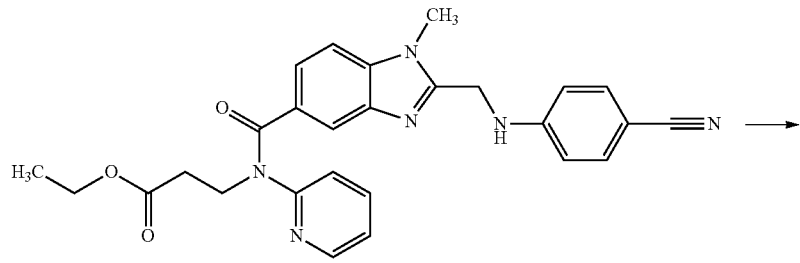

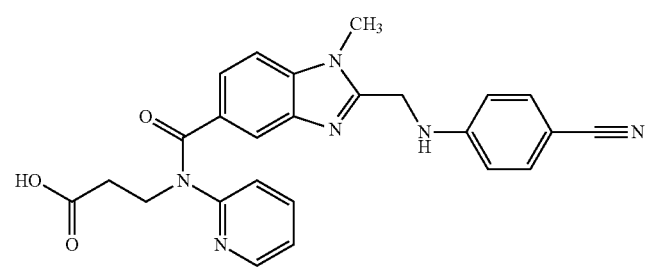

To a solution of sodium hydroxide (50.0 mmol) in 500 mL ethanol and 50 mL water was added 3-({2-[(4-Cyano-phenylamino)-methyl]-1-methyl-1H-benzoimidazole-5-carbonyl}-pyridin-2-yl-amino)-propionic acid ethyl ester (41.4 mmol). The mixture was stirred at room temperature for three hours, then ca. 350 mL ethanol were distilled off, ca. 100 mL water was added and the pH was adjusted to 6. Then diethylether (50 mL) was added and the mixture stirred over night. The product was isolated by filtration and used without further purification.

Yield: 78%

$C_{25}H_{22}N_6O_3$ (454.48)

2b {2-[3-({2-[(4-Cyano-phenylamino)-methyl]-1-methyl-1H-benzoimidazole-5-carbonyl}-pyridin-2-yl-amino)-propionylamino]-ethyl}-carbamic acid tert-butyl ester A solution of the product of 2a (2.20 mmol), 2-(1H-benzotriazole-1-yl)-1,1,3,3-tetramethyluronium tetrafluoroborate (TBTU, 2.20 mmol) and N-methyl-morpholin (2.20 mmol) in dry tetrahydrofuran (100 mL) was stirred at room temperature for 15 minutes. Then (2-amino-ethyl)-carbamic acid tert-butyl ester (2.20 mmol) was added and the mixture stirred at room temperature for another 24 hours. The mixture was then diluted with 40 mL water, the product was isolated through extraction with ethyl acetate and purified by chromatography (silica gel; dichloromethane/methanol 15:1).

Yield: 61%

$C_{32}H_{36}N_8O_4$ (596.68)

Mass spectrum (ESI): $[M+H]^+$=597

$[M+H]^-$=595

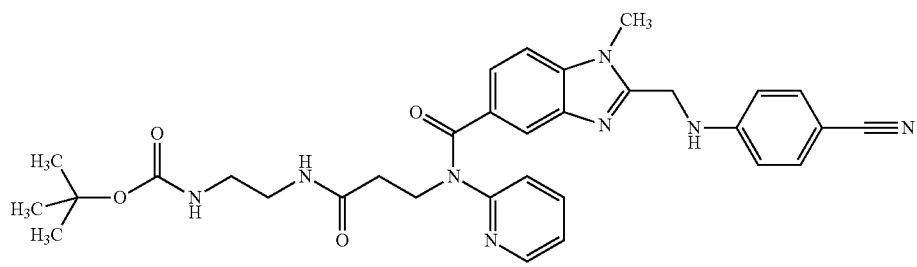 [SMILES: Cn1c(CNc2ccc(C#N)cc2)nc2cc(C(=O)N(CCC(=O)NCCNC(=O)OC(C)(C)C)c3ccccn3)ccc21]

2c 2-[(4-Carbamimidoyl-phenylamino)-methyl]-1-methyl-1H-benzoimidazole-5-carboxylic acid [2-(2-amino-ethylcarbamoyl)-ethyl]pyridin-2-yl-amide

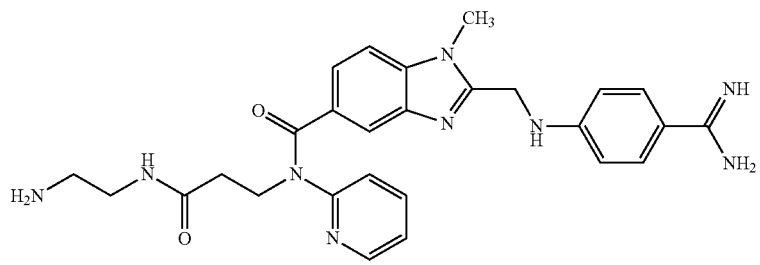 [SMILES: Cn1c(CNc2ccc(C(=N)N)cc2)nc2cc(C(=O)N(CCC(=O)NCCN)c3ccccn3)ccc21]

The product of 2b (1.34 mmol) was added to a saturated HCl solution in dry ethanol (30 mL). The solution was stirred at room temperature for 5 hours, then evaporated to dryness at 30° C. Ethanol (30 mL) and ammonium carbonate (13.0 mmol) were added and the mixture stirred at room temperature over night. The solvent was then evaporated, the residual material was triturated 5 times with ca. 4 mL of a mixture of dichloromethane/methanol (30:1), filtered and evaporated in order to separate the product from inorganic salts.

Yield: 27%
$C_{27}H_{31}N_9O_2$ (513.61)
Mass spectrum (ESI): $[M+Cl]^-=548/50$
$[M+HCl+Cl]^-=584/6$
$[M+H]^+=514$

2. Chemicals
2.1 Chemicals for Reagent Synthesis

| name | specification | supplier | catalogue no. |
| --- | --- | --- | --- |
| 1,4-Benzoquinone | | Fluka | 12309 |
| Bovines Serum Albumin (BSA) | | Serva | 11920 |
| 1,1'-Carbonyl-di-(1,2,4-triazol) | | Fluka | 21861 |
| Citric acid | analytical grade | Riedel-De Haën | 33114 |
| N,N-dimethylformamide (DMF) | for synthesis | Merck | 822275 |
| Ethanol | analytical grade | Baker | 8006 |
| Freund's adjuvant (CFA) | Complete | Sigma | F-5881 |
| Freund's adjuvant (IFA) | Incomplete | Sigma | F-5506 |
| Glycerine | Pure | Merck | 104093 |
| horseradish peroxidase HRP | 25000 U/100 mg | Boehringer Mannheim | 108090 |
| $H_2SO_4$ | analytical grade | Riedel-De Haën | 30743 |
| $KH_2PO_4$ | analytical grade | Merck | 4873 |
| $NaHCO_3$ | analytical grade | Merck | 106329 |
| $Na_2CO_3$ | analytical grade | Merck | 106392 |
| $(NH_4)_2SO_4$ | analytical grade | Merck | 101217 |
| o-phenylene diamine | 30 mg tablet | Sigma | P8412 |
| Sodium perborate | Pure | Riedel-De Haën | 11621 |
| Thymol | Pure | Merck | 8167 |

2.2 Chemicals for ELISA

| Name | Specification | supplier | catalogue no. |
| --- | --- | --- | --- |
| Citric acid | analytical grade | Riedel-De Haën | 33114 |
| $H_2SO_4$ | analytical grade | Riedel-De Haën | 30743 |
| $KH_2PO_4$ | analytical grade | Merck | 4873 |
| $Na_2HPO_4 \cdot 2H_2O$ | analytical grade | Merck | 6580 |
| NaCl | analytical grade | Merck | 6404 |
| NaOH | analytical grade | Merck | 6498 |
| o-phenylene diamine | 30 mg tablet | Sigma | P8412 |
| Sodium perborate | Pure | Riedel-De Haën | 11621 |
| Tween 20 | Pure | Serva | 37470 |

2.3 Buffers for ELISA

| Name | Ingredients | use |
| --- | --- | --- |
| buffer 1 stability: | 0.05M $Na_2HPO_4/KH_2PO_4$ 0.15M NaCl, pH = 7.4 4 weeks at approximately +4° C. | coating |
| buffer 2 stability: | as buffer 1, with 5 g/l BSA 10 days at approximately +4° C. | assay buffer |
| buffer 3 stability: | as buffer 1, with 5 g/l BSA and 0.1 g/L thimerosal 4 weeks at approximately +4° C. | microplate blocking; storage |
| buffer 4 stability: | 0.1M citric acid, adjusted to pH 5.0 with NaOH, 6.5 mmol/L sodium perborate citric acid: 6 months at approximately +4° C. with perborate: 10 days at approximately +4° C. | substrate buffer for o-phenylene diamine |
| wash solution stability: | water, 0.5 g/L Tween 20 10 days at ambient temperature | microplate washing |
| stop reagent stability: | 2.25M $H_2SO_4$ 5 years at ambient temperature | arrests o-phenylene diamine colour development |

Water from an Elgastat Maxima-HPLC ultra pure water processing system was used to prepare buffer solutions.

3. Synthesis of Immunogens

In order to stimulate the immune system of rabbits to produce polyclonal antibodies against dabigatran, three immunogens (lot. nos. GL256, GL258, and GL262) were synthesized by coupling the haptens HAPTEN1 and HAPTEN2 to the carrier protein bovine serum albumin (BSA) using 1,4-benzoquinone or 1,1'-carbonyl-di-(1,2,4-triazol) as coupling reagent.

For the synthesis of GL256, 1,4-benzoquinone was used as a homobifunctional compound with two reactive sites. First it reacts at an acidic pH with amino groups at only one of the two sites and at an alkaline pH at the other site with minimal polymerization. GL258 and GL262 were synthesized using 1,1'-carbonyl-di-(1,2,4-triazol) as coupling reagent with different input ratios of the hapten to the carrier protein.

3.1 Synthesis of GL256

To the solution of 0.75 µMol BSA in 8.5 mL 0.1 M $KH_2PO_4$-buffer (pH=4.5), 0.416 mMol 1,4-benzoquinone (in 1.5 mL ethanol) was added and incubated for 1.5 h in the dark at room temperature. Afterwards the solution passed a sephadex G25 column equilibrated in 0.15 M NaCl to eliminate the excess of 1,4-benzoquinone (final volume 12.5 mL).

2.5 mL (0.15 µMol) of the purified BSA-solution were added slowly under stirring to a solution of the 525 µMol hapten HAPTEN1 dissolved in 2 mL 0.1 M $NaHCO_3$/$Na_2CO_3$-buffer (pH=8.5). During addition of the BSA solution the pH was adjusted to approximately 8.0. The molar input ratio of the hapten and the carrier protein was 3500:1.

After incubation at room temperature over night the immunogen was dialysed 6 times against 1 litre of aqua. dest. Thin-layer chromatography showed that no spots of unbound hapten remained in the hapten-carrier conjugates.

The immunogen was stored frozen in aliquots at −20° C. The degree of substitution of BSA with hapten in the supernatant of the immunogen was about 1:18 as determined by UV absorption spectrometry at 302 nm. The content of immunogen in the final solution was 0.75 mg GL256/mL 3.2 Synthesis of GL258

A solution of 158 µMol HAPTEN2 in 6.3 mL N,N-dimethylformamide (DMF) was prepared at room temperature. 158 µMol 1,1'-carbonyl-di-(1,2,4-triazol) was added and incubated first for 4 hours at 10° C. and afterwards for 30 min at room temperature. The chemical reaction was checked with thin-layer chromatography and was about 20-25%. Then 0.75 µMol BSA were dissolved in 2 mL 0.13 M $NaHCO_3$ and 1 mL N,N-dimethylformamide (DMF) was added dropwise under stirring. The pH was adjusted to approximately 8.3. Afterwards the hapten solution (6.3 mL) and 4 mL 0.13 M $NaHCO_3$ were added dropwise to the BSA solution under stirring and the pH was adjusted to 8.4. The molar input ratio of the hapten and the carrier protein was 210:1 for the immunogen GL258.

After incubation at room temperature over night under stirring conditions, the immunogen was dialysed 6 times against 1 litre of aqua. dest. Thin-layer chromatography showed that no spots of unbound hapten remained in the hapten-carrier conjugates.

The immunogen was stored frozen in aliquots at −20° C. The degree of substitution of BSA with hapten in the supernatant of the immunogen was about 1:5 as determined by UV absorption spectrometry at 302 nm. The content of immunogen in the final solution was 0.28 mg GL258/mL.

3.3 Synthesis of GL262

A solution of 225 µMol HAPTEN2 in 8.75 mL N,N-dimethylformamide (DMF) was prepared at room temperature. 225 µMol 1,1'-carbonyl-di-(1,2,4-triazol) was added and incubated for 4 hours at 10° C. The chemical reaction was checked with thin-layer chromatography and was about 20-25%.

Then 0.49 µMol BSA were dissolved in 2 mL 0.13 M $NaHCO_3$ and 1 mL N,N-dimethylformamide (DMF) was added dropwise under stirring. The pH was adjusted to approximately 8.2. Afterwards the hapten solution (8.75 mL) and 6 mL 0.13 M $NaHCO_3$ were added dropwise to the BSA solution under stirring and the pH was adjusted to 8.3. The molar input ratio of the hapten and the carrier protein was 460:1 for the immunogen GL262.

After incubation at room temperature over night under stirring conditions, the immunogen was dialysed 6 times against 1 litre of aqua. dest. Thin-layer chromatography showed that no spots of unbound hapten remained in the hapten-carrier conjugates.

The immunogen was stored frozen in aliquots at −20° C. The degree of substitution of BSA with hapten in the supernatant of the immunogen was about 1:32 as determined by UV absorption spectrometry at 302 nm. The content of immunogen in the final solution was 0.71 mg GL262/mL 4. Synthesis of Conjugate 4.1 Synthesis of GL261

A solution of 37.4 µMol HAPTEN2 in 1.5 mL N,N-dimethylformamide (DMF) was prepared at room temperature. 37.5 µMol 1,1'-carbonyl-di-(1,2,4-triazol) was added and incubated first for 4 hours at 10° C. and afterwards for 30 min at room temperature. The chemical reaction was checked with thin-layer chromatography and was about 20-25%.

Then 1.125 µMol enzyme horseradish peroxidase (HRP) were dissolved in 0.4 mL 0.13 M $NaHCO_3$ and 0.267 mL N,N-dimethylformamide (DMF) was added dropwise under stirring. The pH was adjusted to approximately 8.2. Afterwards 0.9 mL of the hapten solution (22.5 µMol) and 0.57 mL 0.13 M $NaHCO_3$ were added dropwise to the HRP solution under stirring and the pH was adjusted to 8.4. The molar input ratio of the hapten and the HRP was 20:1 for the HRP conjugate GL261.

After incubation at room temperature over night under stirring conditions, the HRP conjugate was separated from organic solvents and the excess of hapten by gel chromatography. The solution passed a sephadex G25 column equilibrated with 0.1 M phosphate buffer pH 7.0.

The final concentration of hapten-HRP conjugate (tracer, 5.64 mg/mL) was spiked with BSA yielding a concentration of about 10 mg/mL, an equal volume of glycerine to prevent freezing and a thymol crystal to prevent bacterial growth. The tracer solution was labelled as lot no. GL261 and stored in aliquots at −20° C.

The degree of substitution of HRP with hapten was 1:0.2 as determined by UV spectroscopy at 302 nm.

The specific activity of the tracer was measured in BSA-blocked microtiter plates using o-phenylene-diamine (OPD) as substrate and native HRP as reference material. The mixture of diluted HRP standards or the hapten-HRP conjugate and substrate solution were incubated for 30 min in the dark, stopped with sulphuric acid and absorption measured at 490 nm. The remaining activity was 94% of the native HRP and the specific activity of the conjugate formulation in glycerine was 611 U/mL.

Summary of Tracer Specifications:

| | |
|---|---|
| type: | HAPTEN2 - horseradish peroxidase (lot no. GL 261) |
| protein content: | 5.64 mg/mL |
| specific activity: | 108 U/mg 611 U/ml (substrate Guajacol and $H_2O_2$, 25° C.) |
| storage: | at approximately −20° C. |
| working dilution: | 1:40000 |

5. Immunization and Production of Antibodies 5.1 Immunization of Rabbits

Twelve female chinchilla rabbits, 3 months old, were immunized with an emulsion of 100 immunogen GL256, GL258 and GL262 in 0.5 mL 0.9% NaCl solution and 0.5 mL of complete Freund's adjuvant (CFA). Several booster immunizations followed in the next month. For the third immunization 0.5 mL of incomplete Freund's adjuvant (IFA) was used. Each immunization was performed at four subcutaneous and four intramuscular sites.

Group A—Immunogen GL256
Rabbit 1 #50
Rabbit 2 #51
Rabbit 3 #52
Rabbit 4 #53
Group B—Immunogen GL258
Rabbit 5 #54
Rabbit 6 #55
Rabbit 7 #56
Rabbit 8 #57
Group C—Immunogen GL262
Rabbit 9 #46
Rabbit 10 #47
Rabbit 11 #48
Rabbit 12 #49

Immunization Scheme

| Day | |
|---|---|
| Day 1 | First immunization with 100 μg immunogen/mL per animal in CFA |
| Day 29 | Second immunization with 100 μg immunogen/mL per animal in CFA |
| Day 57 | Third immunization with 100 μg immunogen/mL per animal in IFA the rabbit's state of the healthy might change for the worse by the use of immunogens GL256 and GL258 rabbit 7 #56 was not treated |
| Day 67 | First bleeding (2 mL per animal) |
| Day 81 | Fourth immunization with 100 μg immunogen/mL per animal in CFA |
| Day 91 | Second bleeding (25 mL per animal) |
| Day 112 | Fifth immunization with 100 μg immunogen/mL per animal in CFA |
| Day 122 | Assignment of the animal numbers was mislaid Third final bleeding (Exsanguination)* |

*Rabbit no. 1-12 were exsanguinated completely 10 days after the fifth immunization. Exsanguination was performed via a carotid artery under anesthesia with xylazin (Rompun ®, Bayer, Leverkusen, Germany) and ketamine hydrochloride (Ketavet ®, Parke-Davis, Freiburg, Germany).

5.2 Analysis of Rabbit Sera

Serum was prepared by centrifugation of the coagulated rabbit blood. A protein fraction was obtained by ammonium sulphate precipitation and desalting through a Sephadex G25 column.

The individual protein fractions from the rabbit sera were screened for anti-dabigatran titer by a standard ELISA procedure.

Screening-ELISA:

| Step | Procedure |
|---|---|
| A | protein fractions from each bleeding were adsorbed overnight at ambient temperature onto microtiter plates (100 μL/well; 1, 2 or 4 μg/mL) in buffer 1. wash microplates 4 times, 450 μL each block with 250 μL buffer 3 for at least 1 hour |
| B | wash microplates 4 times, 450 μL each |
| C | add to each well of microtiter plate in triplicate: +50 μL buffer 2 +50 μL calibration standards in buffer 2 +25 μL dabigatran-horseradish peroxidase (HRP) conjugate GL 261 (tracer) (1/40000) |
| D | seal microplates with adhesive foil, complete sample distribution for all microplates incubate for 4 h on a shaker at ambient temperature |
| E | wash microplates 4 times, 450 μL each |
| F | add to each well of microtiter plate 100 μL o-phenylene diamine HCl, 2.7 mg/mL (one 30 mg tablet in 11 mL buffer 4) incubate for 30 min in the dark at ambient temperature |
| G | add to each well of microtiter plate 100 μL $H_2SO_4$ (2.25M) shake for 5 minutes |
| H | read absorbance; test-wavelength: 490 nm, reference-wavelength: 650 nm |

5.3 Detection of Anti-Dabigatran Antibodies in Rabbit Sera Last Three Columns: Values are for Dabigatran Bleeding 2

| rabbit | immunogene | coating conc [μg/ml] | conc. [Mol] | [Ext] | [%] |
|---|---|---|---|---|---|
| 1 | #50 | GL256 | 2 | 0 | 1.812 | 100% |
| | | | | 2.E−12 | 1.574 | 87% |
| | | | | 2.E−11 | 0.461 | 25% |
| | | | | 2.E−10 | 0.059 | 3% |
| 2 | #51 | GL256 | 1 | 0 | 2.193 | 100% |
| | | | | 2.E−12 | 2.086 | 95% |
| | | | | 2.E−11 | 1.515 | 69% |
| | | | | 2.E−10 | 0.207 | 9% |
| 3 | #52 | GL256 | 2 | 0 | 1.513 | 100% |
| | | | | 2.E−12 | 1.419 | 94% |
| | | | | 2.E−11 | 0.728 | 48% |
| | | | | 2.E−10 | 0.107 | 7% |
| 4 | #53 | GL256 | 2 | 0 | 1.474 | 100% |
| | | | | 2.E−12 | 1.388 | 94% |
| | | | | 2.E−11 | 0.848 | 58% |
| | | | | 2.E−10 | 0.142 | 10% |
| 5 | #54 | GL258 | 1 | 0 | 2.114 | 100% |
| | | | | 2.E−12 | 1.892 | 89% |
| | | | | 2.E−11 | 0.646 | 31% |
| | | | | 2.E−10 | 0.159 | 8% |
| 6 | #55 | GL258 | 1 | 0 | 1.295 | 100% |
| | | | | 2.E−12 | 0.937 | 72% |
| | | | | 2.E−11 | 0.265 | 20% |
| | | | | 2.E−10 | 0.140 | 11% |
| 7 | #56 | GL258 | 2 | 0 | 1.611 | 100% |
| | | | | 2.E−12 | 1.372 | 85% |
| | | | | 2.E−11 | 0.424 | 26% |
| | | | | 2.E−10 | 0.145 | 9% |
| 8 | #46 | GL258 | 1 | 0 | 1.640 | 100% |
| | | | | 2.E−12 | 1.290 | 79% |
| | | | | 2.E−11 | 0.425 | 26% |
| | | | | 2.E−10 | 0.196 | 12% |
| 9 | #47 | GL262 | 2 | 0 | 1.854 | 100% |
| | | | | 2.E−12 | 1.534 | 83% |
| | | | | 2.E−11 | 0.530 | 29% |
| | | | | 2.E−10 | 0.254 | 14% |
| 10 | #48 | GL262 | 2 | 0 | 1.458 | 100% |
| | | | | 2.E−12 | 1.142 | 78% |
| | | | | 2.E−11 | 0.300 | 21% |
| | | | | 2.E−10 | 0.131 | 9% |
| 11 | #49 | GL262 | 4 | 0 | 1.646 | 100% |
| | | | | 2.E−12 | 1.393 | 85% |
| | | | | 2.E−11 | 0.460 | 28% |
| | | | | 2.E−10 | 0.257 | 16% |
| 12 | #50 | GL262 | 2 | 0 | 1.605 | 100% |
| | | | | 2.E−12 | 1.400 | 87% |
| | | | | 2.E−11 | 0.389 | 24% |
| | | | | 2.E−10 | 0.109 | 7% |

Final Bleeding

| rabbit | immunogene | coating conc [μg/ml] | conc. [Mol] | [Ext] | [%] |
|---|---|---|---|---|---|
| 1 | ? | 1 | 0 | 1.589 | 100% |
|   |   |   | 2.E−12 | 1.442 | 91% |
|   |   |   | 2.E−11 | 0.491 | 31% |
|   |   |   | 2.E−10 | 0.130 | 8% |
| 2 | ? | 1 | 0 | 1.375 | 100% |
|   |   |   | 2.E−12 | 1.041 | 76% |
|   |   |   | 2.E−11 | 0.293 | 21% |
|   |   |   | 2.E−10 | 0.101 | 7% |
| 3 | ? | 1 | 0 | 1.400 | 100% |
|   |   |   | 2.E−12 | 1.081 | 77% |
|   |   |   | 2.E−11 | 0.288 | 21% |
|   |   |   | 2.E−10 | 0.097 | 7% |
| 4 | ? | 1 | 0 | 1.183 | 100% |
|   |   |   | 2.E−12 | 0.882 | 75% |
|   |   |   | 2.E−11 | 0.396 | 33% |
|   |   |   | 2.E−10 | 0.183 | 15% |
| 5 | ? | 1 | 0 | 1.335 | 100% |
|   |   |   | 2.E−12 | 1.066 | 80% |
|   |   |   | 2.E−11 | 0.183 | 14% |
|   |   |   | 2.E−10 | 0.057 | 4% |
| 6 | ? | 1 | 0 | 1.214 | 100% |
|   |   |   | 2.E−12 | 0.976 | 80% |
|   |   |   | 2.E−11 | 0.250 | 21% |
|   |   |   | 2.E−10 | 0.123 | 10% |
| 7 | ? | 2 | 0 | 1.822 | 100% |
|   |   |   | 2.E−12 | 1.702 | 93% |
|   |   |   | 2.E−11 | 0.661 | 36% |
|   |   |   | 2.E−10 | 0.189 | 10% |
| 8 | ? | 2 | 0 | 1.234 | 100% |
|   |   |   | 2.E−12 | 1.085 | 88% |
|   |   |   | 2.E−11 | 0.671 | 54% |
|   |   |   | 2.E−10 | 0.147 | 12% |
| 9 | ? | 1 | 0 | 1.911 | 100% |
|   |   |   | 2.E−12 | 1.862 | 97% |
|   |   |   | 2.E−11 | 0.980 | 51% |
|   |   |   | 2.E−10 | 0.292 | 15% |
| 10 | ? | 1 | 0 | 1.933 | 100% |
|   |   |   | 2.E−12 | 1.891 | 98% |
|   |   |   | 2.E−11 | 1.055 | 55% |
|   |   |   | 2.E−10 | 0.076 | 4% |
| 11 | ? | 1 | 0 | 1.874 | 100% |
|   |   |   | 2.E−12 | 1.817 | 97% |
|   |   |   | 2.E−11 | 1.539 | 82% |
|   |   |   | 2.E−10 | 0.181 | 10% |
| 12 | ? | 2 | 0 | 1.599 | 100% |
|   |   |   | 2.E−12 | 1.425 | 89% |
|   |   |   | 2.E−11 | 0.475 | 30% |
|   |   |   | 2.E−10 | 0.050 | 3% |

After screening of the protein fractions of all rabbits from bleeding 2, it was obvious that rabbit no. 5 (#54) had the highest titre of anti-dabigatran antibodies with the preferred hapten HAPTEN2. Furthermore, it was possible to displace the tracer from the antibody binding sites with only low concentrations of analyte (dabigatran).

For the screening of the final bleeding 3, the displacement of the tracer from the antibody binding site with low concentrations of analyte (dabigatran) was used as main decision criteria, because of the missing information about the immunogen used. Therefore rabbits no. 2, 3 and 5 were used for the further purification.

5.4 Purification of Polyclonal Antibodies

The anti-serum of rabbit no. 5 (#54) bleeding no. 2 and rabbits no. 2, 3 and 5 bleeding no. 3 (final bleeding) was precipitated with ammonium sulphate. The precipitate was centrifuged for 30 min at 10° C. at 4500 U/min, separated from the solution and re-dissolved in Tris buffer. This procedure was repeated. Further purification was performed by affinity chromatography on protein A sepharose FF. The column buffer was 0.01 M Tris pH=7.5 and 0.1 M glycine pH=3.0 was used for elution. Fractions containing the rabbit IgG were combined. Protein concentration was determined by UV spectroscopy at 280 nm.

Summary of Antibody Specifications:

| | |
|---|---|
| immunogen: | HAPTEN2-BSA (lot no. GL258) |
| rabbit: | no. 5 (#54) serum (bleeding no. 2) |
| protein content: | 1.85 mg/mL |
| storage: | at approximately −20° C. |
| immunogen: | HAPTEN1-BSA (GL256) or |
|   | HAPTEN2-BSA (lot no. GL258) or |
|   | HAPTEN2-BSA (lot no. GL262) |
| rabbit: | no. 2 serum collected (final bleeding) |
| protein content: | 3.9 mg/mL |
| storage: | at approximately −20° C. |
| immunogen: | HAPTEN1-BSA (GL256) or |
|   | HAPTEN2-BSA (lot no. GL258) or |
|   | HAPTEN2-BSA (lot no. GL262) |
| rabbit: | no. 3 serum (final bleeding) |
| protein content: | 9.96 mg/mL |
| storage: | at approximately −20° C. |
| immunogen: | HAPTEN1-BSA (GL256) or |
|   | HAPTEN2-BSA (lot no. GL258) or |
|   | HAPTEN2-BSA (lot no. GL262) |
| rabbit: | no. 5 serum (final bleeding) |
| protein content: | 5.72 mg/mL |
| storage: | at approximately −20° C. |

II. neutralization of dabigatran

Two series of experiments were performed to show the effect of the antibodies against dabigatran anticoagulant activity in vitro. The four polyclonal antibodies were received in the laboratory and further tested in human plasma. This was tested in the functional assay, the thrombin clotting time.

Assay Description:

Briefly human plasma is obtained by taking whole blood into 3.13% sodium citrate. This is then centrifuged to obtain platelet free plasma and transferred to a separate tube and frozen until required on the day of the assay. Plasma is thawed at 37° C. on the day of the assay.

The thrombin clotting time is performed as follows. First thrombin is diluted to manufacturer's specification (3 IU/mL thrombin) in the buffer provided (Dade Behring Test kit) and prewarmed to 37° C. It is used within 2 hrs of being prepared. All assays were performed on a commercially available CL4 clotting machine (Behnk Electronics, Norderstadt, Germany). Fifty μL of plasma is pipetted into provided cuvettes with a magnetic stirrer and allowed to stir for 2 min in the well preheated to 37° C. in the CL4 machine. At this point 100 μL of the thrombin solution is added and the time required for the plasma sample to clot is recorded automatically by the CL4. Dabigatran is preincubated for 5 min in plasma in the provided cuvettes, before adding thrombin and starting the measurement. If antibody is also tested (up 50 μL of stock solution), there is a further 5 minute incubation at 37° C. before beginning clotting (i.e. 10 min total incubation with dabigatran, 5 min total incubation with antibody and then clotting is initiated with thrombin).

Initially a dabigatran standard curve was performed by adding increasing concentrations of dabigatran to human plasma and measuring the time to clotting after addition of thrombin (FIG. 1). There was a concentration-dependent increase in the thrombin clotting time with increasing concentrations of dabigatran.

Figure 2:
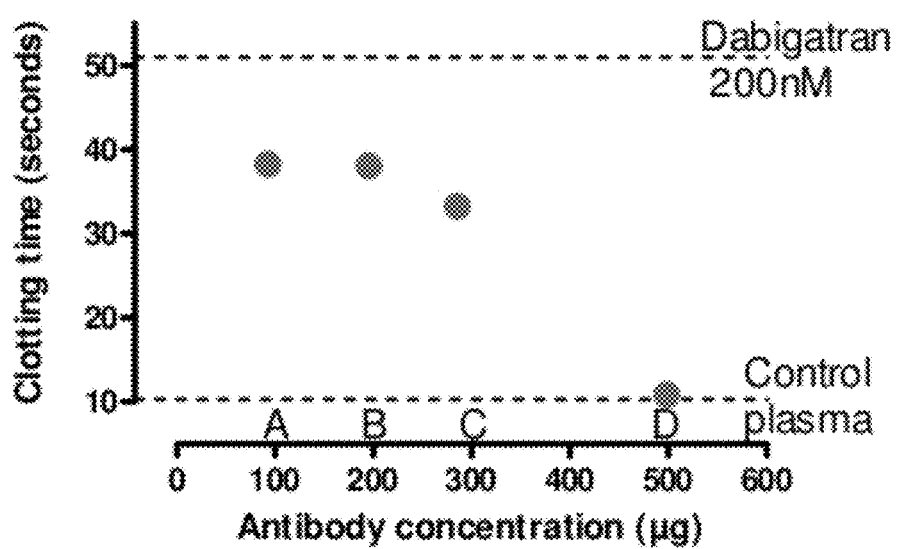
FIG. 2: Four different antibodies to dabigatran (A-D) all neutralized the prolonged clotting time of dabigatran in human plasma. Baseline clotting in human plasma was 10.9 seconds, when 200 nM dabigatran was preincubated with plasma, clotting was prolonged to 51 seconds. Each antibody was added to plasma preincubated with 200 nM of dabigatran and further incubated for 5 min. The thrombin clotting time was then initiated by addition of thrombin. Each antibody could reverse the clotting time of dabigatran to different degrees. The most concentrated solution resulted in the largest reversal of anticoagulant activity.
Figure 3:
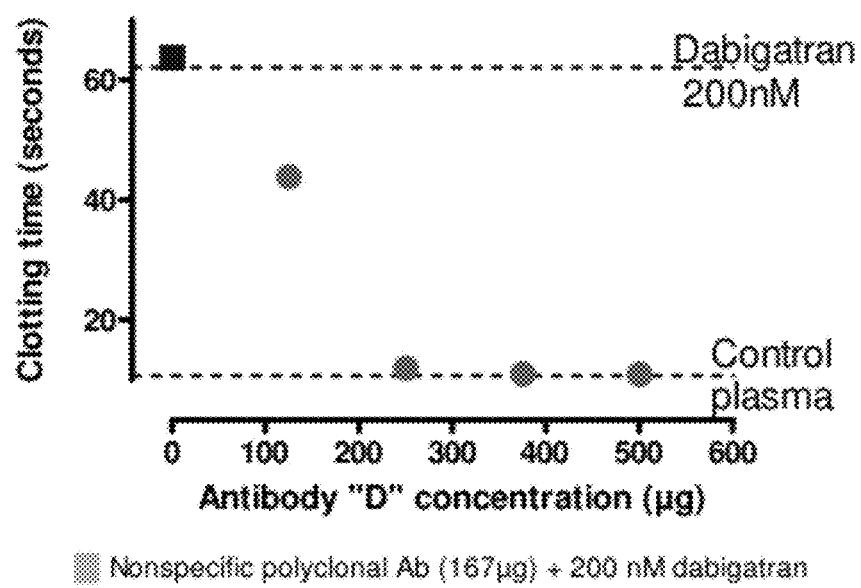
FIG. 3: The effect of increasing concentrations of polyclonal antibody (antibody D) added to human plasma that had been preincubated with 200 nM dabigatran was measured. Baseline clotting time was 11 seconds, addition of dabigatran prolonged clotting to 63.7 seconds. The effect of increasing dilutions of antibody on reversing the prolonged thrombin clotting time with dabigatran was then tested. The lowest concentration reduced the thrombin clotting time to 43.9 seconds. Higher concentrations completely reduced the thrombin clotting time to baseline levels and resulted in complete neutralization of the anticoagulant effect of dabigatran. Addition of a non specific rabbit polyclonal antibody (square) had no effect on reversing the anticoagulant effect of dabigatran.

For the first set of neutralization experiments, a clinically relevant concentration of 200 nM of dabigatran was added to all plasma samples for neutralization. All 4 antibody preparations were able to shorten the time to clotting in plasma containing dabigatran (FIG. 2). The extent of neutralization was related to the concentration of protein in each antibody preparation. The antibody solution with the highest concentration (D) was then serially diluted and tested for the ability to neutralize 200 nM dabigatran anticoagulant activity in a separate set of experiments. It can be seen in FIG. 3, there was a concentration dependent inhibition of dabigatran-induced anticoagulant activity with increasing concentrations of antibody. In addition when a non-specific rabbit polyclonal antibody (blue square) was added to plasma containing dabigatran, it had no ability to neutralise the anticoagulant activity. The concentration dependency and the lack of neutralization of a non specific antibody indicate the reversal of anticoagulation by the antibody is specific for dabigatran.

Figure 4:
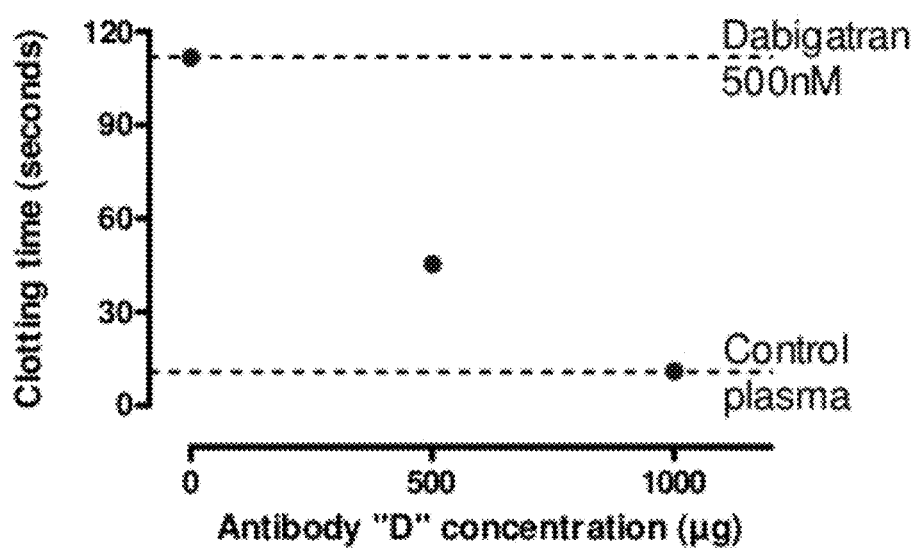
FIG. 4: The effect of increasing concentrations of polyclonal antibody (antibody D) added to human plasma that had been preincubated with 500 nM dabigatran was measured. Baseline clotting time was 10.9 seconds, addition of this higher concentration of dabigatran prolonged clotting to 111.7 seconds (~10-fold increase). The effect of a 1:2 dilution of antibody or stock solution reversed the prolonged thrombin clotting time with dabigatran in a concentration dependent manner. The highest concentration also completely reversed the thrombin clotting time to baseline levels and resulted in complete neutralization of the anticoagulant effect of even supratherapeutic concentrations of dabigatran.

However, these concentrations of dabigatran are clinically relevant, and bleeding or overdoses will probably occur with higher concentrations. Thus the ability of an antibody to inhibit the anticoagulant activity of the highest concentration of dabigatran (500 nM) in the standard curve in FIG. 1 was also tested. FIG. 4 illustrates that antibody D could also inhibit high concentrations of dabigatran.

III. Production and Characterization of Monoclonal Anti-Dabigatran Antibodies

1. Production of Monoclonal Anti-Dabigatran Antibodies and Fabs

Mice were immunized with Hapten1 (see Example 1.1) conjugated to carrier proteins such as hemocyanin and immunoglobulin and hybridomas were generated according to standard procedures. Monoclonal antibodies purified from the culture supernatants bound to dabigatran-protein conjugates and this binding could be competed with dabigatran in solution with half-maximal inhibition at concentrations in the range of 1 to 10 nM. Fabs were generated by papain cleavage of the monoclonal antibodies with subsequent elimination of the Fc domain via Protein A.

The variable regions from the heavy and light chains of the mouse antibodies were cloned and sequenced using standard methods. The sequences were confirmed by protein analysis by mass spectrometry and N-terminal sequencing of the antibodies. DNA constructs encoding chimeric antibodies comprising the specific mouse variable regions and human IgG constant regions were generated and protein was expressed in HEK 293T cells and purified.

2. Characterization of Monoclonal Anti-Dabigatran Antibodies and Fabs

The sequences of the variable domains of three monoclonal antibody clones are depicted in FIGS. 5 and 6. The amino acid sequences of the variable domains of clone 13 are depicted in FIG. 5 (DBG 13 VH, heavy chain, SEQ ID NO: 16) and FIG. 6 (DBG 13 VK, light chain, SEQ ID NO: 17). The amino acid sequences of the variable domains of clone 14 are depicted in FIG. 5 (DBG 14 VH, heavy chain, SEQ ID NO: 18) and FIG. 6 (DBG 14 VK, light chain, SEQ ID NO: 19).The amino acid sequences of the variable domains of clone 22 are depicted in FIG. 5 (DBG 22 VH, heavy chain, SEQ ID NO: 20) and FIG. 6 (DBG 22 VK, light chain, SEQ ID NO: 21).

Figure 7:
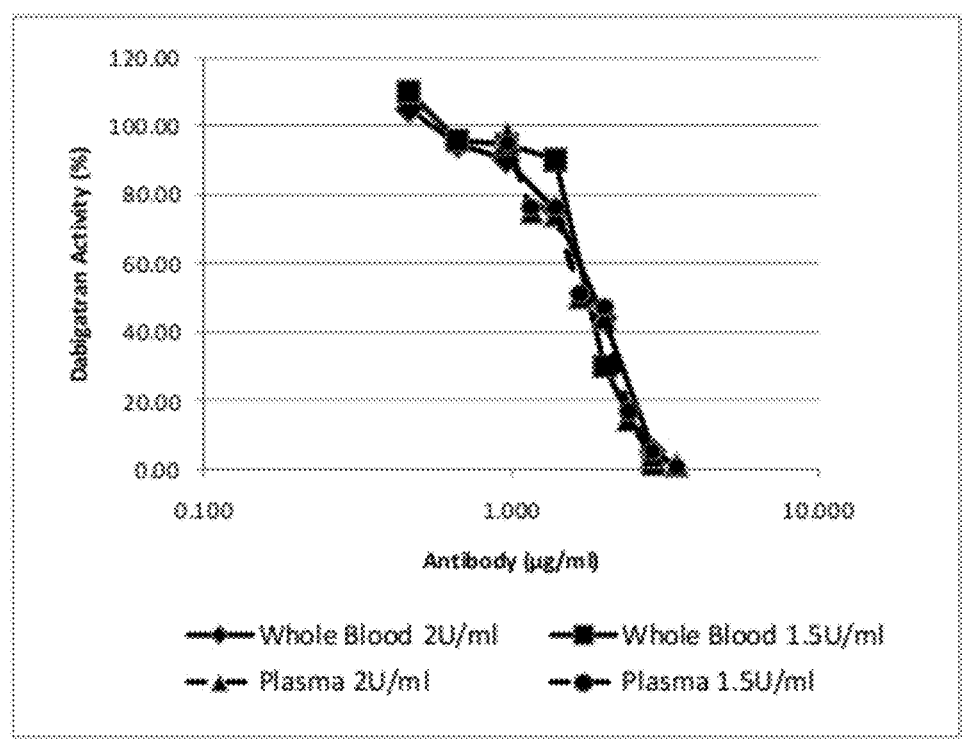
FIG. 7: A mouse monoclonal antibody (Clone 22) reverses the anticoagulant effect of dabigatran in human plasma and in human whole blood. Increasing concentrations of mouse antibody were added to human plasma or whole blood that had been preincubated with 30 nM dabigatran. The assay was initiated by the addition of 1.5-2 U/mL of thrombin and clotting time was measured. 100% dabigatran activity was defined as the difference in clotting time in the presence and absence of compound. The antibody dose dependently inhibited the dabigatran mediated prolongation of clotting time.
Figure 8:
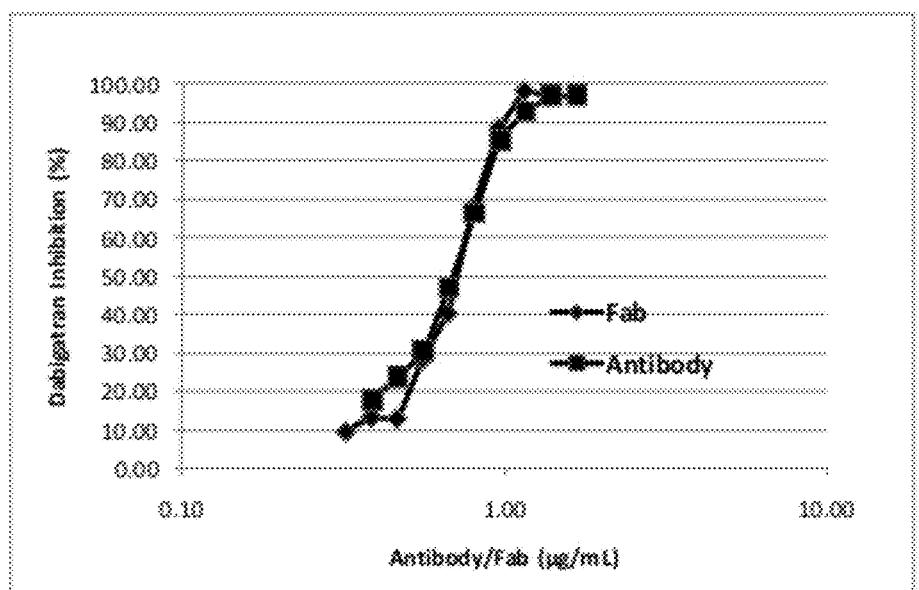
FIG. 8: A mouse Fab generated from the Clone 22 antibody reverses the anticoagulant effect of dabigatran in human plasma. Increasing concentrations of mouse Fab were added to human plasma that had been preincubated with 7 nM dabigatran. The intact antibody was also tested as a positive control. The assay was initiated by the addition of 0.4 U/mL of thrombin and clotting time was measured. 100% inhibition was defined as the complete block of the dabigatran mediated increase in clotting time. The Fab dose dependently inhibited the dabigatran induced prolongation in clotting time in human plasma.

The mouse monoclonal antibody clone 22 was tested for its ability to neutralize dabigatran anticoagulant activity in human plasma in the thrombin clotting time assay outlined in Example II. The antibody completely reversed the dabigatran-mediated prolongation of thrombin dependent clotting in human plasma in a dose dependent manner (FIG. 7). The antibody also effectively inhibited dabigatran function in human whole blood. A Fab generated from this antibody blocked dabigatran activity in human plasma demonstrating that monovalent antigen binding domains can neutralize compound anticoagulant activity. (FIG. 8).

Figure 9:
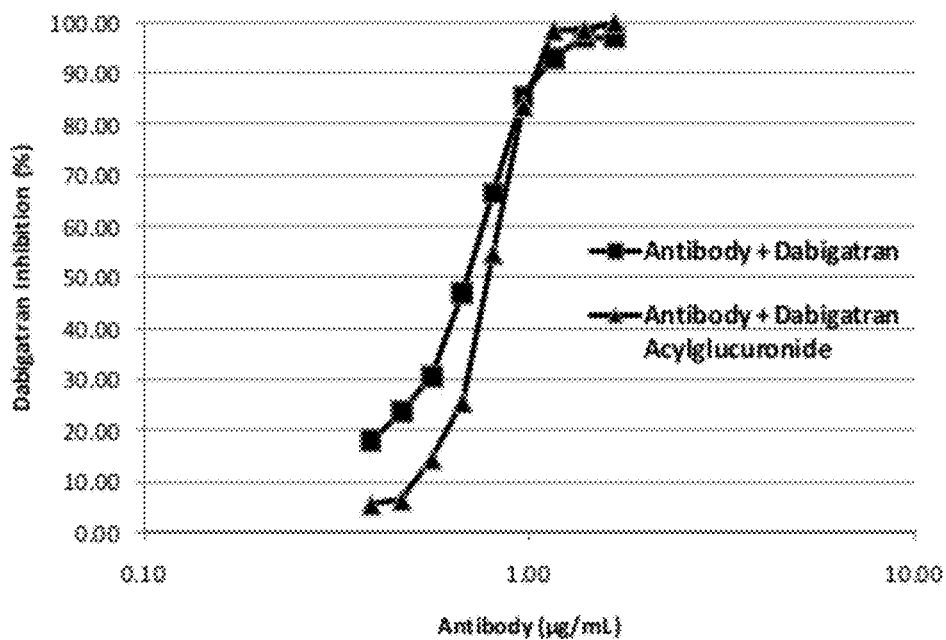
FIG. 9: A mouse monoclonal antibody (Clone 22) reverses the anticoagulant effect of dabigatran acylglucuronide in human plasma. Increasing concentrations of mouse antibody were added to human plasma that had been preincubated with 7 nM of dabigatran acylglucuronide or dabigatran. The assay was initiated by the addition of 0.4 U/mL of thrombin and clotting time was measured. 100% inhibition was defined as the complete block of the compound mediated increase in clotting time. The antibody dose dependently inhibited the dabigatran acylglucuronide induced prolongation in clotting time in human plasma.

The major metabolic pathway of dabigatran in humans is through the glucuronidation of the carboxylate moiety. Dabigatran acylglucuronides have been shown to be pharmacologically active (Ebner et al., Drug Metab. Dispos. 2010, 38(9):1567-75). To test whether the mouse monoclonal antibody clone 22 could neutralize these metabolites, dabigatran acylglucuronides were purified from the urine of rhesus monkeys treated with dabigatran and evalulated in the thrombin clotting time assay. The antibody dose dependently reversed the dabigatran acylglucuronide-mediated prolongation of thrombin dependent clotting in human plasma with similar potency to that seen with dabigatran (FIG. 9). Thus the antibody is effective in blocking the anticoagulant activity of dabigatran metabolites found in humans.

The affinities of the Fab and the mouse-human chimeric antibodies comprising the variable domains of clones 22, 13 and 14 and human immunoglobulin constant regions (light chain constant region: SEQ ID NO: 44; heavy chain constant region: SEQ ID NO: 45) were determined using Kinexa technology. A constant concentration of Fab or chimeric antibody was incubated with various concentrations of dabigatran until equilibrium was reached. After this incubation the concentration of free antibody was determined by capturing the antibody on Neutravidin beads coupled with a Biotin-conjugated dabigatran analog. The captured Fab was detected with an anti-Mouse IgG (Fab specific) F(ab')2 fragment labeled with FITC. The captured chimeric antibodies were detected with an anti-human IgG conjugated with Cy5. The dissociation constants were calculated using a 1:1 binding model. The results from these experiments are summarized in the table below.

Affinity of Anti-Dabigatran Antibodies

| Antibody | Apparent $K_d$ |
|---|---|
| Clone 22 Fab | 48 pM |
| Clone 22 Chimeric Ab | 34 pM |
| Clone 13 Chimeric Ab | 60 pM |
| Clone 14 Chimeric Ab | 46 pM |

Both the Fab and the chimeric antibodies bind dabigatran with high affinity.

3. Generation of Humanized Monoclonal Anti-Dabigatran Antibodies and Fabs

In order to reduce potential immunogenicity following administration in man the mouse monoclonal antibodies were 'humanized.' Human framework sequences were selected for the mouse leads based on the framework homology, CDR structure, conserved canonical residues, conserved interface packing residues and other parameters. The specific substitution of amino acid residues in these framework positions can improve various aspects of antibody performance including binding affinity and/or stability, over that demonstrated in humanized antibodies formed by "direct swap" of CDRs or HVLs into the human germline framework regions. Fabs that showed better or equal binding and improved expression as compared to the chimeric parent Fab were selected for further characterization. The amino acid sequences of the variable domains of the humanized Fabs are depicted in FIG. 5 (Eng VH 14, SEQ ID NO: 22; ENG VH 15, SEQ ID NO: 24; and ENG VH 31, SEQ ID NO: 26) and in FIG. 6 (Eng VK 11, SEQ ID NO: 23; ENG VK 17, SEQ ID NO: 25; and ENG VK 18, SEQ ID NO: 27). A Fab comprising Eng VH 15 and Eng VK 18 (light chain: SEQ ID NO: 37; heavy chain: SEQ ID NO: 36) was directly expressed in CHO cells and purified using Kappa select and Protein G resins.

The Fab comprising Eng VH15 and Eng VK 18 was also converted to a full length IgG in the IgG1KO format (light chain: SEQ ID NO: 35; heavy chain: SEQ ID NO: 40). IgG1KO (knock-out of effector functions) has two mutations in the Fc region, Leu234Ala and Leu235Ala, which reduce effector function such as FcgR and complement binding. The IgG format is described in the literature (see for example Hezareh et al. (2001) Journal of Virology 75: 12161-12168). The humanized anti-dabigatran antibodies optionally include specific amino acid substitutions in the consensus or germline framework regions. The 18/15 antibody was expressed in HEK 293T cells or CHO cells and purified. Fab fragments were generated by either Lys-C or papain cleavage of the intact antibody and purified with elimination of the Fc domain via Protein A.

4. Characterization of Anti-Dabigatran Fabs

Figure 10:
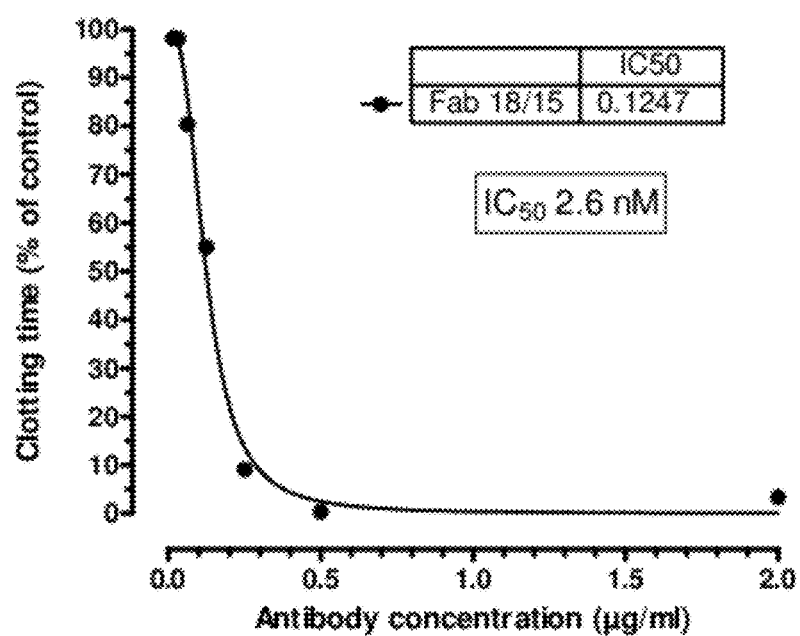
FIG. 10: A humanized Fab (Fab 18/15) reverses the anticoagulant effect of dabigatran in human plasma. Increasing concentrations of Fab 18/15 were added to human plasma that had been preincubated with 7 nM dabigatran. The assay was initiated by the addition of 0.4 U/mL of thrombin and clotting time was measured. 100% inhibition was defined as the complete block of the dabigatran mediated increase in clotting time. The Fab dose dependently inhibited the dabigatran induced prolongation in clotting time in human plasma.

18/15 Fab fragment generated by Lys-C cleavage of the intact antibody was tested for its ability to neutralize dabigatran anticoagulant activity in human plasma in the thrombin clotting time assay outlined in Example II. The Fab completely reversed the dabigatran-mediated prolongation of thrombin dependent clotting in human plasma is a dose dependent manner with an $IC_{50}$ of 2.6 nM (FIG. 10). The directly expressed Fab fragment and the Fab fragment generated by papain cleavage of the intact antibody also neutralized dabigatran anticoagulant activity with $IC_{50}$'s of 2.6 and 2.7 nM, respectively.

The affinity of 18/15 Fab generated by Lys-C cleavage of the intact antibody and the directly expressed Fab were determined on a BIAcore instrument utilizing SPR technology. The Fabs were preincubated with increasing concentrations of dabigatran for 30 minutes at room temperature. The mixture was flowed over a sensor chip coated with immobilized biotin-conjugated dabigatran analog and the binding of free Fab was monitored. Using this solution competition assay design, the $K_D$ values of the Fabs for dabigatran were determined to be 0.16 pM for the Lys-C generated and 0.45 pM for the directly expressed Fabs.

In Vivo Experiments with Fab Generated by Papain Cleavage

Rats (male Wistar, ~300 g) were anesthetized with pentobarbital as a bolus (60 mg/kg i.p.) and a continuous infusion for maintenance anesthesia (20 mg/kg/hr i.p.) and were placed on a 37° C. heating pad to maintain internal body temperature. The carotid artery was isolated and cannulated for blood sampling and the right jugular vein for substance administration. Dabigatran was initiated as a bolus (0.3 μM/kg) and followed by an infusion (0.1 μM/kg/hr) over 20 min to achieve steady state plasma levels. After 20 min, the Fab was injected i.v. as a single bolus at either equimolar or half equimolar concentrations via the left jugular vein. Blood samples (1/10 dilution in 3.13% sodium citrate) are taken at baseline (−20, −2 min) and at varying intervals for 30 min post Fab injection.

The anticoagulant effects of dabigatran were measured as whole blood clotting times, including the thrombin time (TT) and activated partial thromboplastin time (aPTT). Briefly, the thrombin time is performed on a coagulometer by adding 50 μL whole blood into a well that is prewarmed to 37° C. Thrombin (Siemens Healthcare, Marburg, Germany) in concentrations of 3.0 U/mL is added (100 μL volume) and the time required to clot the sample is measured. The whole blood aPTT is performed by prewarming 50 μL whole blood to 37° C. in a coagulometer and adding 50 μL aPTT reagent (Roche Diagnostics, Mannheim, Germany) for 3 min. Clotting time is initiated by the addition of 50 μL 0.025M prewarmed (37° C.) calcium chloride. The time required to clot the whole blood sample is then recorded.

Figure 11:
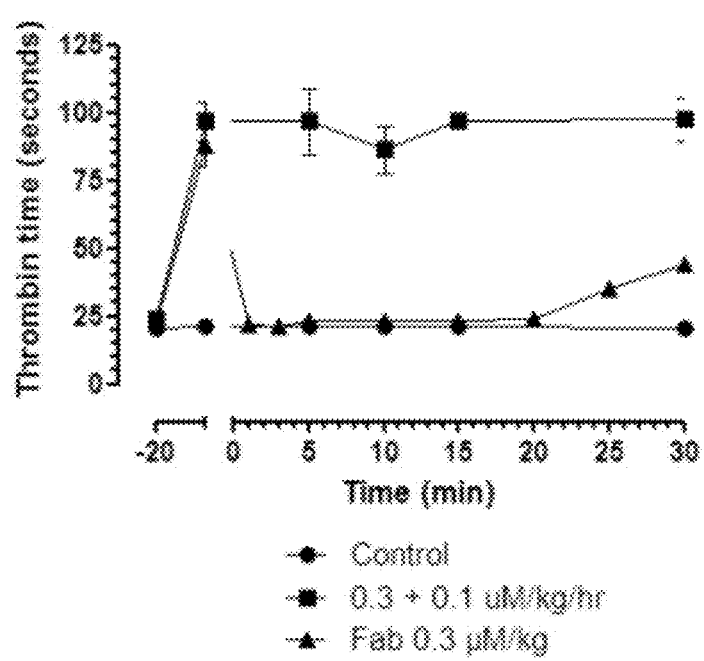
FIG. 11: The ex vivo whole blood thrombin clotting time (3.0 U/mL thrombin) in rats receiving dabigatran as a continuous infusion with a bolus administration of equimolar Fab at t=0. The line with solid circles represents vehicle treatment without drug. The line with solid squares represents dabigatran anticoagulant activity without Fab. The line with solid triangles represents anticoagulant activity after administration of Fab. Data are expressed as the mean±SE, n=4 animals per treatment group.
Figure 12:
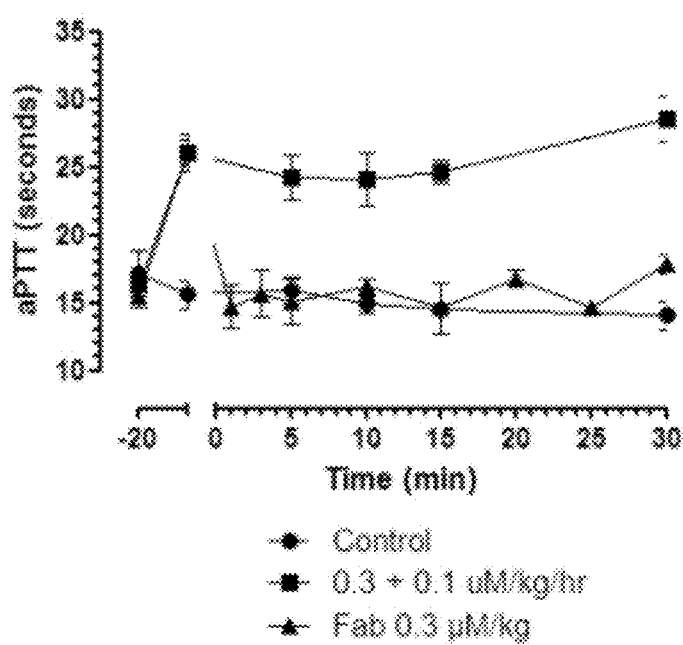
FIG. 12: The ex vivo whole blood aPTT in rats receiving dabigatran as a continuous infusion with a bolus administration of equimolar Fab at t=0. The solid circles represents vehicle treatment without drug. The line with solid squares represents dabigatran anticoagulant activity without Fab. The line with solid triangles represents anticoagulant activity after administration of Fab. Data are expressed as the mean±SE, n=4 animals per treatment group.

The results of 18/15 Fab (light chain: SEQ ID NO: 37, heavy chain Fd fragment: SEQ ID NO: 41; produced by papain cleavage of full immuoglobulin expressed in CHO cells) given as a single i.v. injection at an equimolar dose to dabigatran are shown in FIGS. 11 and 12. There was a rapid, almost immediate inhibition of dabigatran anticoagulant activity, measured both as TT (FIG. 11) and aPTT (FIG. 12) in this model. Within one minute of injection, dabigatran anticoagulant activity was completely neutralized back to baseline levels. This was maintained for over 20 min, despite the ongoing continuous infusion of i.v. dabigatran.

Figure 13:
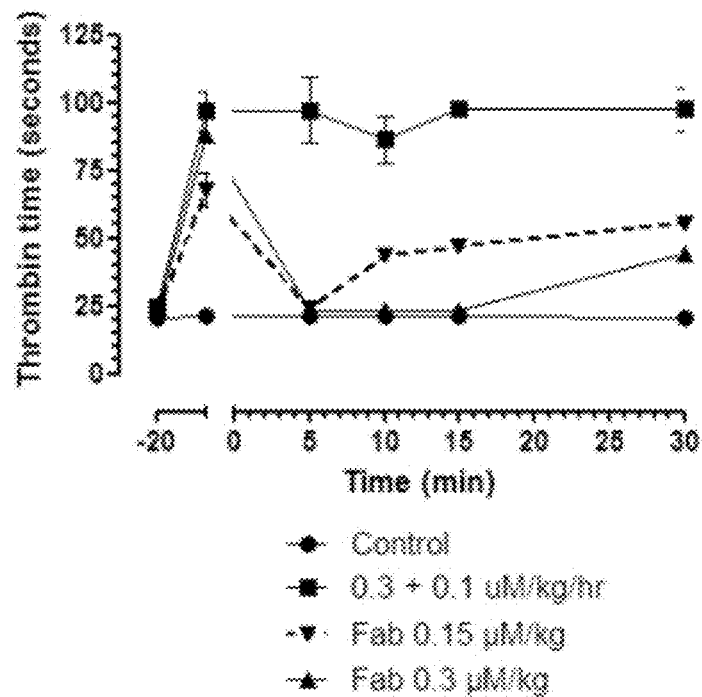
FIG. 13: The ex vivo whole blood thrombin clotting time (3.0 U/mL thrombin) in rats receiving dabigatran as a continuous infusion with a bolus administration of increasing doses of Fab at t=0. The line with solid circles represents vehicle treatment without drug. The line with solid squares represents dabigatran anticoagulant activity without Fab. The line with solid triangles represents anticoagulant activity after equimolar administration of Fab and the dashed line 50% of equimolar dose. Data are expressed as the mean±SE, n=4 animals per treatment group.
Figure 14:
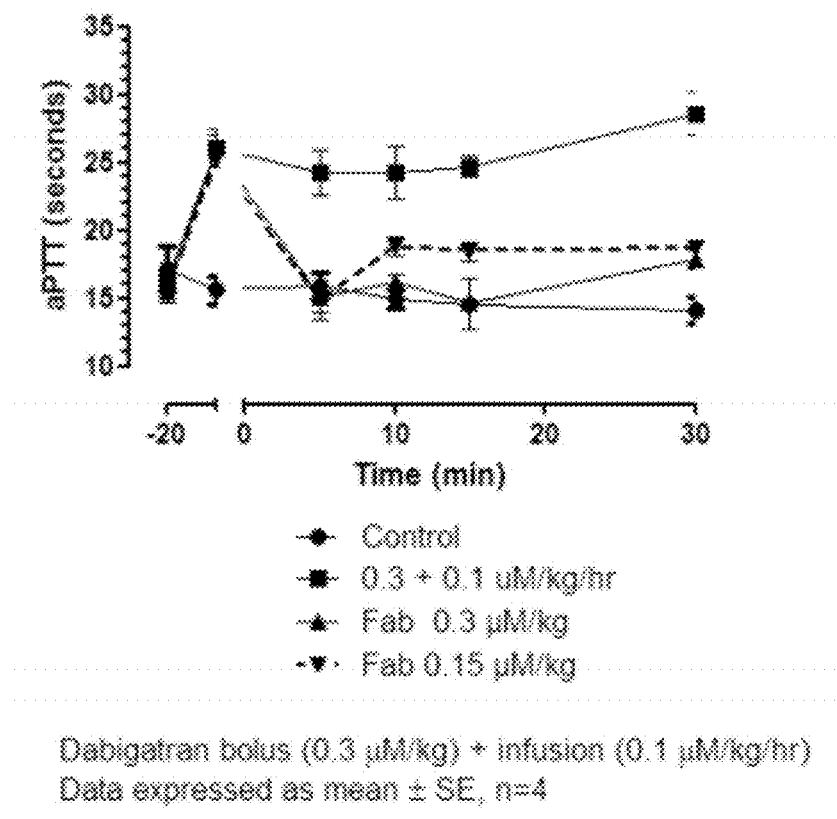
FIG. 14: The ex vivo whole blood aPTT in rats receiving dabigatran as a continuous infusion with a bolus administration of increasing doses of Fab at t=0. The solid circles represents vehicle treatment without drug. The line with solid squares represents dabigatran anticoagulant activity without Fab. The line with solid triangles represents anticoagulant activity after administration of equimolar Fab and the dashed line 50% of equimolar dose. Data are expressed as the mean±SE, n=4 animals per treatment group.

When the lower dose, half the molar dose of dabigatran was given, there was also an initial reduction of both TT (FIG. 13) and the aPTT (FIG. 14). This was however, not maintained as long as the higher dose under the conditions of the ongoing continuos infusion of dabigatran.

Thus, these results demonstrate a predictable, dose-dependent and very rapid neutralization of dabigatran anticoagulant activity after a single i.v. administration of anti-dabigatran Fab in this animal model.

What we claim:

1. An isolated antibody molecule of capable of binding to and neutralizing the activity of dabigatran, which comprises a heavy chain variable domain with a CDR1 selected from the group consisting of SEQ ID NO: 1 and SEQ ID NO: 2, a CDR2 selected from the group consisting of SEQ ID NO: 3, SEQ ID NO: 4, SEQ ID NO: 5, SEQ ID NO: 6, SEQ ID NO: 7, and SEQ ID NO: 8, and a CDR3 selected from the group consisting of SEQ ID NO: 9 and SEQ ID NO: 10, and a light chain variable domain with a CDR1 selected from the group consisting of SEQ ID NO: 11, SEQ ID NO: 12, and SEQ ID NO: 13, a CDR2 of SEQ ID NO: 14, and a CDR3 of SEQ ID NO: 15.

2. The antibody molecule of claim 1 which is capable of neutralizing the activity of dabigatran and 1-O-acylglucuronide of dabigatran.

3. The antibody molecule of claim 1 which comprises a heavy chain variable domain with a CDR1 of SEQ ID NO: 1, a CDR2 selected from the group consisting of SEQ ID NO: 6, SEQ ID NO: 7, and SEQ ID NO: 8, a CDR3 of SEQ ID NO: 10, and a light chain variable domain with a CDR1 of SEQ ID NO: 13, a CDR2 of SEQ ID NO: 14, and a CDR3 of SEQ ID NO: 15.

4. The antibody molecule of claim 1 which comprises a heavy chain variable domain selected from the group consisting of SEQ ID NOs: 16, 18, 20, 22, 24, and 26, and a light chain variable domain selected from the group consisting of SEQ ID Nos: 17, 19, 21, 23, 25, and 27.

5. The antibody molecule of claim 4 which comprises a heavy chain variable domain of SEQ ID NO: 16, and a light chain variable domain of SEQ ID No: 17, or a heavy chain variable domain of SEQ ID NO: 18, and a light chain variable domain of SEQ ID No: 19, or a heavy chain variable domain of SEQ ID NO: 20, and a light chain variable domain of SEQ ID No: 21, or a heavy chain variable domain of SEQ ID No:

22, and a light chain variable domain of SEQ ID No: 23, or a heavy chain variable domain of SEQ ID NO: 24, and a light chain variable domain of SEQ ID No: 25, or a heavy chain variable domain of SEQ ID NO: 24, and a light chain variable domain of SEQ ID No: 27, or a heavy chain variable domain of SEQ ID NO: 26, and a light chain variable domain of SEQ ID No: 27.

6. The antibody molecule of claim 1 which is a polyclonal antibody, a monoclonal antibody, a human antibody, a humanized antibody, a chimeric antibody, a fragment of an antibody, a single chain antibody, a Small Modular Immunopharmaceutical (SMIP), a or a diabody.

7. The antibody molecule of claim 6 which is a scFv, wherein the heavy chain variable domain and the light chain variable domain are linked to each other through a linker peptide selected from the group consisting of SEQ ID NO: 28, SEQ ID NO: 29, SEQ ID NO: 30, and SEQ ID NO: 31.

8. The antibody molecule of claim 7 which comprises SEQ ID NO: 32, or SEQ ID NO: 33.

9. The antibody molecule of claim 6 having a heavy chain comprising SEQ ID NO: 34 or SEQ ID NO: 40, and a light chain comprising SEQ ID NO: 35, or having a heavy chain comprising SEQ ID NO: 42, and a light chain comprising SEQ ID NO: 43.

10. The antibody of claim 6 which is a Fab molecule having a Fd fragment comprising SEQ ID NO: 36, SEQ ID NO: 38, or SEQ ID NO: 41, and a light chain comprising SEQ ID NO: 37 or SEQ ID NO: 39.

11. The antibody of claim 6, wherein the antibody fragment is a Fab, Fab', or F(ab')$_2$ fragment.

12. The antibody of claim 6, wherein the single chain antibody is a single chain variable fragment (scFv).

13. A kit comprising an antibody of claim 1, or a pharmaceutical composition thereof.

14. A kit comprising:
a. an antibody of claim 1, or a pharmaceutical composition thereof;
b. a container; and
c. a label.

15. A kit comprising an antibody of claim 1, and dabigatran, dabigatran etexilate, a prodrug of dabigatran or a pharmaceutically acceptable salt thereof.

16. The kit according to claim 15, wherein the form of dabigatran, dabigatran etexilate, a prodrug of dabigatran or a pharmaceutically acceptable salt thereof is in the form of a solid, liquid or gel.

17. The kit according to claim 15, wherein the pharmaceutically acceptable salt of dabigatran etexilate is a mesylate salt.

18. The kit according to claim 15 or 17, wherein the strength per dosage unit of the dabigatran, dabigatran etexilate, a prodrug of dabigatran or a pharmaceutically acceptable salt thereof is between 75 mg and 300 mg, either QD or BID.

19. A kit comprising:
a. an antibody of claim 1, or a pharmaceutical composition thereof;
b. a pharmaceutical composition of dabigatran, dabigatran etexilate, a prodrug of dabigatran or a pharmaceutically acceptable salt thereof;
c. a container; and
d. a label.

20. The kit according to claim 19, wherein the form of dabigatran, dabigatran etexilate, a prodrug of dabigatran or a pharmaceutically acceptable salt thereof is in the form of a solid, liquid or gel.

21. The kit according to claim 19, wherein the pharmaceutically acceptable salt of dabigatran etexilate is a mesylate salt.

22. The kit according to claim 19 or 21, wherein the strength per dosage unit of the dabigatran, dabigatran etexilate, a prodrug of dabigatran or a pharmaceutically acceptable salt thereof is between 75 mg and 300 mg, either QD or BID.

23. A kit comprising:
a. a first pharmaceutical composition comprising dabigatran, dabigatran etexilate, a prodrug of dabigatran or a pharmaceutically acceptable salt thereof;
b. a second pharmaceutical composition comprising an antibody of claim 1;
c. instructions for separate administration of said first and second pharmaceutical compositions to a patient,
wherein said first and second pharmaceutical compositions are contained in separate containers and said second pharmaceutical composition is administered to a patient requiring neutralization or partial neutralization of dabigatran or 1-O-acylglucuronide of dabigatran.

24. A method for preventing or treating side effects of anticoagulant therapy, or of an overdosing event in anticoagulant therapy, comprising administering an effective amount of an antibody molecule of claim 1 to a patient in need thereof, wherein the anticoagulant therapy comprises dabigatran, dabigatran etexilate, a prodrug of dabigatran or a pharmaceutically acceptable salt thereof.

25. The method according to claim 24, wherein the side effect is a bleeding event.

26. A method of manufacturing an antibody molecule of claim 1, comprising
a. providing a host cell comprising one or more nucleic acids encoding said antibody molecule in functional association with an expression control sequence,
b. cultivating said host cell, and
c. recovering the antibody molecule from the cell culture.

27. A method for neutralizing or partially neutralizing dabigatran or 1-O-acylglucuronide of dabigatran in a patient being treated with dabigatran, dabigatran etexilate, a prodrug of dabigatran or a pharmaceutically acceptable salt thereof, comprising administering an antibody of claim 1, or a pharmaceutical composition thereof.

28. A method for neutralizing or partially neutralizing dabigatran or 1-O-acylglucuronide of dabigatran in a patient comprising:
a. confirming that a patient was being treated with dabigatran, dabigatran etexilate, a prodrug of dabigatran or a pharmaceutically acceptable salt thereof, and the amount that was taken by the patient;
b. neutralizing dabigatran or 1-O-acylglucuronide with an antibody of claim 1 prior to performing a clotting or coagulation test or assay wherein dabigatran or the 1-O-acylglucuronide of dabigatran would interfere with the accurate read out of the test or assay results;
c. performing the clotting or coagulation test or assay on a sample taken from the patient to determine the level of clot formation without dabigatran or 1-O-acylglucuronide of dabigatran present; and
d. adjusting an amount of dabigatran, dabigatran etexilate, a prodrug of dabigatran or a pharmaceutically acceptable salt thereof administered to the patient in order to achieve the appropriate balance between clot formation and degradation in a patient.

29. The method according to claim 27 or 28, wherein the amount of antibody to dabigatran or 1-O-acylglucuronide of dabigatran is in the molar ratio of between 0.1 and 100.

30. The method according to claim 29, wherein the amount of antibody to dabigatran or 1-O-acylglucuronide of dabigatran is in the molar ratio of between 0.1 and 10.

31. The method according to claim 28, wherein the accurate read out of the test or assay result is an accurate read out of fibrinogen levels, activated protein C resistance or related tests.

\* \* \* \* \*

SEQUENCE LISTING

```
<160> NUMBER OF SEQ ID NOS: 45

<210> SEQ ID NO 1
<211> LENGTH: 10
<212> TYPE: PRT
<213> ORGANISM: Artificial Sequence
<220> FEATURE:
<223> OTHER INFORMATION: VH CDR1 A

<400> SEQUENCE: 1

Gly Phe Ser Leu Thr Ser Tyr Ile Val Asp
1               5                   10

<210> SEQ ID NO 2
<211> LENGTH: 10
<212> TYPE: PRT
<213> ORGANISM: Artificial Sequence
<220> FEATURE:
<223> OTHER INFORMATION: VH CDR 1B
```

```
<400> SEQUENCE: 2

Gly Phe Ser Leu Thr Asn Tyr Ile Val Asp
1               5                   10

<210> SEQ ID NO 3
<211> LENGTH: 16
<212> TYPE: PRT
<213> ORGANISM: Artificial Sequence
<220> FEATURE:
<223> OTHER INFORMATION: VH CDR2 A

<400> SEQUENCE: 3

Val Ile Trp Gly Ala Gly Ser Thr Asn Tyr Asn Ser Ala Leu Lys Ser
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: VH CDR2 B

<400> SEQUENCE: 4

Val Ile Trp Ala Gly Gly Ser Thr Ser Tyr Asn Ser Ala Leu Arg Ser
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: VH CDR2 C

<400> SEQUENCE: 5

Val Ile Trp Ala Gly Gly Ser Thr Asn Tyr Asn Ser Ala Leu Arg Ser
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: VH CDR2 D

<400> SEQUENCE: 6

Val Ile Trp Ala Gly Gly Ser Thr Arg Tyr Asn Ser Ala Leu Arg Ser
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: VH CDR2 E

<400> SEQUENCE: 7

Val Ile Trp Ala Gly Gly Ser Thr Gly Tyr Asn Ser Ala Leu Arg Ser
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: VH CDR2 F

<400> SEQUENCE: 8
```

```
Val Ile Trp Ala Gly Gly Ser Thr Ala Tyr Asn Ser Ala Leu Arg Ser
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: VH CDR3 A

<400> SEQUENCE: 9

Ala Ala Tyr Tyr Ser Tyr Tyr Asn Phe Asp Gly Phe Ala Tyr
1               5                   10

<210> SEQ ID NO 10
<211> LENGTH: 14
<212> TYPE: PRT
<213> ORGANISM: Artificial Sequence
<220> FEATURE:
<223> OTHER INFORMATION: VH CDR3 B

<400> SEQUENCE: 10

Ala Ala Tyr Tyr Ser Tyr Tyr Asn Tyr Asp Gly Phe Ala Tyr
1               5                   10

<210> SEQ ID NO 11
<211> LENGTH: 16
<212> TYPE: PRT
<213> ORGANISM: Artificial Sequence
<220> FEATURE:
<223> OTHER INFORMATION: VK CDR1 A

<400> SEQUENCE: 11

Lys Ser Ser Gln Ser Leu Leu Tyr Thr Asn Gly Lys Thr Tyr Leu Tyr
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: VK CDR1 B

<400> SEQUENCE: 12

Lys Ser Ser Gln Ser Leu Leu Tyr Thr Asn Gly Lys Ser Tyr Leu Tyr
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: VK CDR1 C

<400> SEQUENCE: 13

Lys Ser Ser Gln Ser Leu Leu Tyr Thr Asp Gly Lys Thr Tyr Leu Tyr
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: VK CDR2

<400> SEQUENCE: 14

Leu Val Ser Lys Leu Asp Ser
1               5
```

<210> SEQ ID NO 15
<211> LENGTH: 9
<212> TYPE: PRT
<213> ORGANISM: Artificial Sequence
<220> FEATURE:
<223> OTHER INFORMATION: VK CDR3

<400> SEQUENCE: 15

Leu Gln Ser Thr His Phe Pro His Thr
1               5

<210> SEQ ID NO 16
<211> LENGTH: 122
<212> TYPE: PRT
<213> ORGANISM: Mus musculus

<400> SEQUENCE: 16

Asp Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Ile Val Asp Trp Val Arg Gln Ser Pro Gly Lys Gly Leu Glu Trp Leu
            35                  40                  45

Gly Val Ile Trp Gly Ala Gly Ser Thr Asn Tyr Asn Ser Ala Leu Lys
        50                  55                  60

Ser Arg Leu Asn Ile Thr Lys Asp Asn Ser Lys Asn Gln Val Phe Leu
65                  70                  75                  80

Lys Met Asn Ser Leu Gln Thr Asp Asp Thr Ala Ile Tyr Tyr Cys Ala
                85                  90                  95

Ser Ala Ala Tyr Tyr Ser Tyr Tyr Asn Phe Asp Gly Phe Ala Tyr Trp
            100                 105                 110

Gly Gln Gly Thr Leu Val Thr Val Ser Ala
        115                 120

<210> SEQ ID NO 17
<211> LENGTH: 112
<212> TYPE: PRT
<213> ORGANISM: Mus musculus

<400> SEQUENCE: 17

Asp Ile Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
                20                  25                  30

Asn Gly Lys Thr Tyr Leu Tyr Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Thr His Phe Pro His Thr Phe Gly Gly Gly Thr Lys Leu Glu Ile Lys
            100                 105                 110

<210> SEQ ID NO 18
<211> LENGTH: 122
<212> TYPE: PRT
<213> ORGANISM: Mus musculus

```
<400> SEQUENCE: 18

Gln Val Gln Leu Glu Gln Ser Gly Pro Gly Leu Val Ala Pro Ser Gln
1               5                   10                  15

Arg Leu Ser Ile Thr Cys Thr Val Ser Gly Phe Ser Leu Thr Asn Tyr
            20                  25                  30

Ile Val Asp Trp Val Arg Gln Ser Pro Gly Lys Gly Leu Glu Trp Leu
        35                  40                  45

Gly Val Ile Trp Ala Gly Gly Ser Thr Ser Tyr Asn Ser Ala Leu Arg
    50                  55                  60

Ser Arg Leu Ser Ile Thr Lys Asn Asn Ser Lys Ser Gln Val Phe Leu
65                  70                  75                  80

Gln Met Asn Ser Leu Gln Thr Asp Asp Thr Ala Thr Tyr Tyr Cys Ala
                85                  90                  95

Ser Ala Ala Tyr Tyr Ser Tyr Tyr Asn Tyr Asp Gly Phe Ala Tyr Trp
            100                 105                 110

Gly Gln Gly Thr Leu Val Thr Val Ser Ala
        115                 120

<210> SEQ ID NO 19
<211> LENGTH: 112
<212> TYPE: PRT
<213> ORGANISM: Mus musculus

<400> SEQUENCE: 19

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Lys Ser Tyr Leu Tyr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Ile Tyr Tyr Cys Leu Gln Ser
                85                  90                  95

Thr His Phe Pro His Thr Phe Gly Gly Gly Thr Lys Leu Glu Ile Lys
            100                 105                 110

<210> SEQ ID NO 20
<211> LENGTH: 122
<212> TYPE: PRT
<213> ORGANISM: Mus musculus

<400> SEQUENCE: 20

Gln Val Gln Leu Glu Gln Ser Gly Pro Gly Leu Val Ala Pro Ser Gln
1               5                   10                  15

Arg Leu Ser Ile Thr Cys Thr Val Ser Gly Phe Ser Leu Thr Ser Tyr
            20                  25                  30

Ile Val Asp Trp Val Arg Gln Ser Pro Gly Lys Gly Leu Glu Trp Leu
        35                  40                  45

Gly Val Ile Trp Ala Gly Gly Ser Thr Asn Tyr Asn Ser Ala Leu Arg
    50                  55                  60

Ser Arg Leu Ser Ile Thr Lys Ser Asn Ser Lys Ser Gln Val Phe Leu
65                  70                  75                  80

Gln Met Asn Ser Leu Gln Thr Asp Asp Thr Ala Ile Tyr Tyr Cys Ala
```

```
                    85                  90                  95
Ser Ala Ala Tyr Tyr Ser Tyr Tyr Asn Tyr Asp Gly Phe Ala Tyr Trp
                100                 105                 110

Gly Gln Gly Thr Leu Val Thr Val Ser Ala
        115                 120

<210> SEQ ID NO 21
<211> LENGTH: 112
<212> TYPE: PRT
<213> ORGANISM: Mus musculus

<400> SEQUENCE: 21

Asp Val Val Met Thr Gln Thr Pro Leu Thr Leu Ser Val Thr Ile Gly
1               5                   10                  15

Gln Pro Ala Ser Ile Ser Cys Lys Ser Gln Ser Leu Leu Tyr Thr
            20                  25                  30

Asn Gly Lys Thr Tyr Leu Tyr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Leu Gln Ser
                85                  90                  95

Thr His Phe Pro His Thr Phe Gly Gly Gly Thr Lys Leu Glu Ile Lys
                100                 105                 110

<210> SEQ ID NO 22
<211> LENGTH: 122
<212> TYPE: PRT
<213> ORGANISM: Artificial Sequence
<220> FEATURE:
<223> OTHER INFORMATION: Engineered Antibody Sequence, Heavy Chain
      Variable Domain ENG VH 14

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ile Val Asp Trp Ile Arg Gln Pro Pro Gly Lys Gly Leu Glu Trp Ile
        35                  40                  45

Gly Val Ile Trp Ala Gly Gly Ser Thr Arg Tyr Asn Ser Ala Leu Arg
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ala Ala Tyr Tyr Ser Tyr Tyr Asn Tyr Asp Gly Phe Ala Tyr Trp
                100                 105                 110

Gly Gln Gly Thr Leu Val Thr Val Ser Ser
        115                 120

<210> SEQ ID NO 23
<211> LENGTH: 112
<212> TYPE: PRT
<213> ORGANISM: Artificial Sequence
<220> FEATURE:
<223> OTHER INFORMATION: Engineered Antibody Sequence, Light Chain
      Variable Domain ENG VK 11
```

<400> SEQUENCE: 23

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Thr
            20                  25                  30

Asp Gly Lys Thr Tyr Leu Tyr Trp Phe Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Leu Gln Ser
                85                  90                  95

Thr His Phe Pro His Thr Phe Gly Gly Gly Thr Lys Val Glu Ile Lys
            100                 105                 110

<210> SEQ ID NO 24
<211> LENGTH: 122
<212> TYPE: PRT
<213> ORGANISM: Artificial Sequence
<220> FEATURE:
<223> OTHER INFORMATION: Engineered Antibody Sequence, Heavy Chain
      Variable Domain ENG VH 15

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ile Val Asp Trp Ile Arg Gln Pro Pro Gly Lys Gly Leu Glu Trp Ile
        35                  40                  45

Gly Val Ile Trp Ala Gly Gly Ser Thr Gly Tyr Asn Ser Ala Leu Arg
    50                  55                  60

Ser Arg Val Ser Ile Thr Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ala Ala Tyr Tyr Ser Tyr Tyr Asn Tyr Asp Gly Phe Ala Tyr Trp
            100                 105                 110

Gly Gln Gly Thr Leu Val Thr Val Ser Ser
        115                 120

<210> SEQ ID NO 25
<211> LENGTH: 112
<212> TYPE: PRT
<213> ORGANISM: Artificial Sequence
<220> FEATURE:
<223> OTHER INFORMATION: Engineered Antibody Sequence, Light Chain
      Variable Domain, ENG VK 17

<400> SEQUENCE: 25

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Thr
            20                  25                  30

Asp Gly Lys Thr Tyr Leu Tyr Trp Phe Gln Gln Arg Pro Gly Gln Ser
        35                  40                  45

Pro Lys Arg Leu Ile Tyr Leu Val Ser Lys Leu Asp Ser Gly Val Pro

```
                50              55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Leu Gln Ser
                 85                  90                  95

Thr His Phe Pro His Thr Phe Gly Gly Gly Thr Lys Val Glu Ile Lys
            100                 105                 110

<210> SEQ ID NO 26
<211> LENGTH: 122
<212> TYPE: PRT
<213> ORGANISM: Artificial Sequence
<220> FEATURE:
<223> OTHER INFORMATION: Engineered Antibody Sequence, Heavy Chain
      Variable Domain ENG VH 31

<400> SEQUENCE: 26

Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Ser Tyr
             20                  25                  30

Ile Val Asp Trp Ile Arg Gln Pro Pro Gly Lys Gly Leu Glu Trp Leu
         35                  40                  45

Gly Val Ile Trp Ala Gly Gly Ser Thr Ala Tyr Asn Ser Ala Leu Arg
     50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Ile Tyr Tyr Cys Ala
                 85                  90                  95

Ser Ala Ala Tyr Tyr Ser Tyr Tyr Asn Tyr Asp Gly Phe Ala Tyr Trp
            100                 105                 110

Gly Gln Gly Thr Leu Val Thr Val Ser Ser
        115                 120

<210> SEQ ID NO 27
<211> LENGTH: 112
<212> TYPE: PRT
<213> ORGANISM: Artificial Sequence
<220> FEATURE:
<223> OTHER INFORMATION: Engineered Antibody Sequence, Light Chain
      Variable Domain, ENG VK 18

<400> SEQUENCE: 27

Asp Val Val Met Thr Gln Ser Pro Leu Ser Leu Pro Val Thr Leu Gly
  1               5                  10                  15

Gln Pro Ala Ser Ile Ser Cys Lys Ser Ser Gln Ser Leu Leu Tyr Thr
             20                  25                  30

Asp Gly Lys Thr Tyr Leu Tyr Trp Phe Leu Gln Arg Pro Gly Gln Ser
         35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Ser
                 85                  90                  95

Thr His Phe Pro His Thr Phe Gly Gly Gly Thr Lys Val Glu Ile Lys
            100                 105                 110

<210> SEQ ID NO 28
```

-continued

```
<211> LENGTH: 15
<212> TYPE: PRT
<213> ORGANISM: Artificial Sequence
<220> FEATURE:
<223> OTHER INFORMATION: Linker

<400> SEQUENCE: 28

Gly Gly Gly Gly Ser Gly Gly Gly Ser Gly Gly Gly Gly Ser
1               5                   10                  15

<210> SEQ ID NO 29
<211> LENGTH: 25
<212> TYPE: PRT
<213> ORGANISM: Artificial Sequence
<220> FEATURE:
<223> OTHER INFORMATION: Linker

<400> SEQUENCE: 29

Ser Ser Ala Asp Asp Ala Lys Lys Asp Ala Ala Lys Lys Asp Ala
1               5                   10                  15

Lys Lys Asp Asp Ala Lys Lys Asp Gly
            20                  25

<210> SEQ ID NO 30
<211> LENGTH: 21
<212> TYPE: PRT
<213> ORGANISM: Artificial Sequence
<220> FEATURE:
<223> OTHER INFORMATION: Linker

<400> SEQUENCE: 30

Ser Pro Asn Gly Ala Ser His Ser Ser Ala Ser Gln Thr Gly Ser
1               5                   10                  15

Ala Ser Gly Ser Gln
            20

<210> SEQ ID NO 31
<211> LENGTH: 18
<212> TYPE: PRT
<213> ORGANISM: Artificial Sequence
<220> FEATURE:
<223> OTHER INFORMATION: Linker

<400> SEQUENCE: 31

Gly Ser Thr Ser Gly Ser Gly Lys Pro Gly Ser Gly Glu Gly Ser Thr
1               5                   10                  15

Lys Gly

<210> SEQ ID NO 32
<211> LENGTH: 251
<212> TYPE: PRT
<213> ORGANISM: Artificial Sequence
<220> FEATURE:
<223> OTHER INFORMATION: Engineered Antibody Sequence, scFv

<400> SEQUENCE: 32

Met Ala Asp Val Val Met Thr Gln Ser Pro Leu Ser Leu Pro Val Thr
1               5                   10                  15

Leu Gly Gln Pro Ala Ser Ile Ser Cys Lys Ser Ser Gln Ser Leu Leu
            20                  25                  30

Tyr Thr Asp Gly Lys Thr Tyr Leu Tyr Trp Phe Leu Gln Arg Pro Gly
        35                  40                  45

Gln Ser Pro Arg Arg Leu Ile Tyr Leu Val Ser Lys Leu Asp Ser Gly
    50                  55                  60
```

```
Val Pro Asp Arg Phe Ser Gly Ser Gly Ser Gly Thr Asp Phe Thr Leu
 65                  70                  75                  80

Lys Ile Ser Arg Val Glu Ala Glu Asp Val Gly Val Tyr Tyr Cys Leu
                 85                  90                  95

Gln Ser Thr His Phe Pro His Thr Phe Gly Gly Gly Thr Lys Val Glu
            100                 105                 110

Ile Lys Gly Gly Gly Gly Ser Gly Gly Gly Gly Ser Gly Gly Gly Gly
        115                 120                 125

Ser Gln Val Gln Leu Gln Glu Ser Gly Pro Gly Leu Val Lys Pro Ser
    130                 135                 140

Glu Thr Leu Ser Leu Thr Cys Thr Val Ser Gly Phe Ser Leu Thr Ser
145                 150                 155                 160

Tyr Ile Val Asp Trp Ile Arg Gln Pro Pro Gly Lys Gly Leu Glu Trp
                165                 170                 175

Ile Gly Val Ile Trp Ala Gly Gly Ser Thr Gly Tyr Asn Ser Ala Leu
            180                 185                 190

Arg Ser Arg Val Ser Ile Thr Lys Asp Thr Ser Lys Asn Gln Phe Ser
        195                 200                 205

Leu Lys Leu Ser Ser Val Thr Ala Ala Asp Thr Ala Val Tyr Tyr Cys
    210                 215                 220

Ala Ser Ala Ala Tyr Tyr Ser Tyr Tyr Asn Tyr Asp Gly Phe Ala Tyr
225                 230                 235                 240

Trp Gly Gln Gly Thr Leu Val Thr Val Ser Ser
                245                 250

<210> SEQ ID NO 33
<211> LENGTH: 251
<212> TYPE: PRT
<213> ORGANISM: Artificial Sequence
<220> FEATURE:
<223> OTHER INFORMATION: Engineered Antibody Sequence, scFv2

<400> SEQUENCE: 33

Met Ala Gln Val Gln Leu Gln Glu Ser Gly Pro Gly Leu Val Lys Pro
1               5                  10                  15

Ser Glu Thr Leu Ser Leu Thr Cys Thr Val Ser Gly Phe Ser Leu Thr
                 20                  25                  30

Ser Tyr Ile Val Asp Trp Ile Arg Gln Pro Pro Gly Lys Gly Leu Glu
             35                  40                  45

Trp Ile Gly Val Ile Trp Ala Gly Gly Ser Thr Gly Tyr Asn Ser Ala
     50                  55                  60

Leu Arg Ser Arg Val Ser Ile Thr Lys Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Ser Ala Ala Tyr Tyr Ser Tyr Tyr Asn Tyr Asp Gly Phe Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Asp Val Val Met Thr
    130                 135                 140

Gln Ser Pro Leu Ser Leu Pro Val Thr Leu Gly Gln Pro Ala Ser Ile
145                 150                 155                 160

Ser Cys Lys Ser Ser Gln Ser Leu Leu Tyr Thr Asp Gly Lys Thr Tyr
                165                 170                 175

Leu Tyr Trp Phe Leu Gln Arg Pro Gly Gln Ser Pro Arg Arg Leu Ile
```

```
                    180                 185                 190
Tyr Leu Val Ser Lys Leu Asp Ser Gly Val Pro Asp Arg Phe Ser Gly
                195                 200                 205

Ser Gly Ser Gly Thr Asp Phe Thr Leu Lys Ile Ser Arg Val Glu Ala
        210                 215                 220

Glu Asp Val Gly Val Tyr Tyr Cys Leu Gln Ser Thr His Phe Pro His
225                 230                 235                 240

Thr Phe Gly Gly Gly Thr Lys Val Glu Ile Lys
                245                 250

<210> SEQ ID NO 34
<211> LENGTH: 452
<212> TYPE: PRT
<213> ORGANISM: Artificial Sequence
<220> FEATURE:
<223> OTHER INFORMATION: Engineered Antibody Sequence, IgG1 Heavy Chain

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ile Val Asp Trp Ile Arg Gln Pro Pro Gly Lys Gly Leu Glu Trp Ile
        35                  40                  45

Gly Val Ile Trp Ala Gly Gly Ser Thr Gly Tyr Asn Ser Ala Leu Arg
    50                  55                  60

Ser Arg Val Ser Ile Thr Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ala Ala Tyr Tyr Ser Tyr Tyr Asn Tyr Asp Gly Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300
```

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 35
<211> LENGTH: 219
<212> TYPE: PRT
<213> ORGANISM: Artificial Sequence
<220> FEATURE:
<223> OTHER INFORMATION: Engineered Antibody Sequence, IgG1 Light Chain

<400> SEQUENCE: 35

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Thr
            20                  25                  30

Asp Gly Lys Thr Tyr Leu Tyr Trp Phe Leu Gln Arg Pro Gly Gln Ser
        35                  40                  45

Pro Arg Arg Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ser
                85                  90                  95

Thr His Phe Pro His Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 36
<211> LENGTH: 225
<212> TYPE: PRT
<213> ORGANISM: Artificial Sequence
<220> FEATURE:
<223> OTHER INFORMATION: Engineered Antibody Sequence, Fab Fd

<400> SEQUENCE: 36

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ile Val Asp Trp Ile Arg Gln Pro Pro Gly Lys Gly Leu Glu Trp Ile
        35                  40                  45

Gly Val Ile Trp Ala Gly Gly Ser Thr Gly Tyr Asn Ser Ala Leu Arg
    50                  55                  60

Ser Arg Val Ser Ile Thr Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ala Ala Tyr Tyr Ser Tyr Tyr Asn Tyr Asp Gly Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225
```

<210> SEQ ID NO 37
<211> LENGTH: 219
<212> TYPE: PRT
<213> ORGANISM: Artificial Sequence
<220> FEATURE:
<223> OTHER INFORMATION: Engineered Antibody Sequence, Fab Light Chain

<400> SEQUENCE: 37

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Thr
            20                  25                  30

Asp Gly Lys Thr Tyr Leu Tyr Trp Phe Leu Gln Arg Pro Gly Gln Ser
        35                  40                  45

Pro Arg Arg Leu Ile Tyr Leu Val Ser Lys Leu Asp Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Ser
                 85                  90                  95

Thr His Phe Pro His Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 38
<211> LENGTH: 226
<212> TYPE: PRT
<213> ORGANISM: Artificial Sequence
<220> FEATURE:
<223> OTHER INFORMATION: Engineered Antibody Sequence, Fab Fd

<400> SEQUENCE: 38

```
Ala Gln Val Gln Leu Gln Glu Ser Gly Pro Gly Leu Val Lys Pro Ser
  1               5                  10                  15

Glu Thr Leu Ser Leu Thr Cys Thr Val Ser Gly Phe Ser Leu Thr Ser
                 20                  25                  30

Tyr Ile Val Asp Trp Ile Arg Gln Pro Pro Gly Lys Gly Leu Glu Trp
            35                  40                  45

Ile Gly Val Ile Trp Ala Gly Gly Ser Thr Gly Tyr Asn Ser Ala Leu
 50                  55                  60

Arg Ser Arg Val Ser Ile Thr Lys Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Ser Ala Ala Tyr Tyr Ser Tyr Tyr Asn Tyr Asp Gly Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
```

Ser Cys
225

<210> SEQ ID NO 39
<211> LENGTH: 220
<212> TYPE: PRT
<213> ORGANISM: Artificial Sequence
<220> FEATURE:
<223> OTHER INFORMATION: Engineered Antibody Sequence, Fab Light Chain

<400> SEQUENCE: 39

Ala Asp Val Val Met Thr Gln Ser Pro Leu Ser Leu Pro Val Thr Leu
1               5                   10                  15

Gly Gln Pro Ala Ser Ile Ser Cys Lys Ser Ser Gln Ser Leu Leu Tyr
            20                  25                  30

Thr Asp Gly Lys Thr Tyr Leu Tyr Trp Phe Leu Gln Arg Pro Gly Gln
        35                  40                  45

Ser Pro Arg Arg Leu Ile Tyr Leu Val Ser Lys Leu Asp Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Leu Gln
                85                  90                  95

Ser Thr His Phe Pro His Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 40
<211> LENGTH: 452
<212> TYPE: PRT
<213> ORGANISM: Artificial Sequence
<220> FEATURE:
<223> OTHER INFORMATION: Engineered Antibody Sequence, IgG1 Heavy Chain

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ile Val Asp Trp Ile Arg Gln Pro Pro Gly Lys Gly Leu Glu Trp Ile
        35                  40                  45

Gly Val Ile Trp Ala Gly Gly Ser Thr Gly Tyr Asn Ser Ala Leu Arg
    50                  55                  60

Ser Arg Val Ser Ile Thr Lys Asp Thr Ser Lys Asn Gln Phe Ser Leu

```
            65                  70                  75                  80
Lys Leu Ser Ser Val Thr Ala Ala Asp Thr Ala Val Tyr Tyr Cys Ala
                    85                  90                  95

Ser Ala Ala Tyr Tyr Ser Tyr Tyr Asn Tyr Asp Gly Phe Ala Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 41
<211> LENGTH: 229
<212> TYPE: PRT
<213> ORGANISM: Artificial
<220> FEATURE:
```

<223> OTHER INFORMATION: Engineered Antibody Sequence, Fab Fd

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ile Val Asp Trp Ile Arg Gln Pro Pro Gly Lys Gly Leu Glu Trp Ile
        35                  40                  45

Gly Val Ile Trp Ala Gly Gly Ser Thr Gly Tyr Asn Ser Ala Leu Arg
50                  55                  60

Ser Arg Val Ser Ile Thr Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ala Ala Tyr Tyr Ser Tyr Tyr Asn Tyr Asp Gly Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His
225

<210> SEQ ID NO 42
<211> LENGTH: 452
<212> TYPE: PRT
<213> ORGANISM: Artificial
<220> FEATURE:
<223> OTHER INFORMATION: Mouse/Human Chimeric IgG Heavy Chain

<400> SEQUENCE: 42

Gln Val Gln Leu Glu Gln Ser Gly Pro Gly Leu Val Ala Pro Ser Gln
1               5                   10                  15

Arg Leu Ser Ile Thr Cys Thr Val Ser Gly Phe Ser Leu Thr Ser Tyr
            20                  25                  30

Ile Val Asp Trp Val Arg Gln Ser Pro Gly Lys Gly Leu Glu Trp Leu
        35                  40                  45

Gly Val Ile Trp Ala Gly Gly Ser Thr Asn Tyr Asn Ser Ala Leu Arg
50                  55                  60

Ser Arg Leu Ser Ile Thr Lys Ser Asn Ser Lys Ser Gln Val Phe Leu
65                  70                  75                  80

Gln Met Asn Ser Leu Gln Thr Asp Asp Thr Ala Ile Tyr Tyr Cys Ala
                85                  90                  95

Ser Ala Ala Tyr Tyr Ser Tyr Tyr Asn Tyr Asp Gly Phe Ala Tyr Trp
            100                 105                 110

```
Gly Gln Gly Thr Leu Val Thr Val Ser Ala Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 43
<211> LENGTH: 219
<212> TYPE: PRT
<213> ORGANISM: Artificial
<220> FEATURE:
<223> OTHER INFORMATION: Mouse/Human Chimeric IgG Light Chain

<400> SEQUENCE: 43

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
```

```
                    20                  25                  30
Asn Gly Lys Thr Tyr Leu Tyr Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Leu Gln Ser
                85                  90                  95

Thr His Phe Pro His Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 44
<211> LENGTH: 107
<212> TYPE: PRT
<213> ORGANISM: Homo Sapiens

<400> SEQUENCE: 44

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 45
<211> LENGTH: 330
<212> TYPE: PRT
<213> ORGANISM: Homo Sapiens

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
        50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Ala Ala Gly Gly Pro Ser Val Phe Leu Phe Pro Pro
            115             120             125

Lys Pro Lys Asp Thr Leu Met Ile Ser Arg Thr Pro Glu Val Thr Cys
        130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
        210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
        290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```